US008987416B2

(12) United States Patent  
Paslin

(10) Patent No.: US 8,987,416 B2  
(45) Date of Patent: Mar. 24, 2015

(54) VIRAL FUSION PROTEIN TREATMENT FOR CCR8 MEDIATED DISEASES

(71) Applicant: David A. Paslin, San Mateo, CA (US)

(72) Inventor: David A. Paslin, San Mateo, CA (US)

( * ) Notice: Subject to any disclaimer, the term of this patent is extended or adjusted under 35 U.S.C. 154(b) by 0 days.

(21) Appl. No.: 13/962,757

(22) Filed: Aug. 8, 2013

(65) Prior Publication Data

US 2015/0044273 A1 Feb. 12, 2015

(51) Int. Cl.
| | |
|---|---|
| *C07K 14/065* | (2006.01) |
| *C07K 14/005* | (2006.01) |
| *A61K 38/16* | (2006.01) |
| *A61K 9/127* | (2006.01) |
| *A61N 1/32* | (2006.01) |
| *A61K 9/00* | (2006.01) |
| *A61K 9/14* | (2006.01) |

(52) U.S. Cl.
CPC ............. *C07K 14/005* (2013.01); *A61K 38/162* (2013.01); *A61K 9/127* (2013.01); *A61N 1/327* (2013.01); *A61K 9/0019* (2013.01); *A61K 9/14* (2013.01); *A61K 9/0014* (2013.01); *C07K 2319/21* (2013.01); *A61K 9/0021* (2013.01); *C07K 2319/10* (2013.01); *Y10S 530/826* (2013.01)
USPC .......................................... 530/350; 530/826

(58) Field of Classification Search
None
See application file for complete search history.

(56) References Cited

U.S. PATENT DOCUMENTS

| | | | | |
|---|---|---|---|---|
| 4,554,101 | A | 11/1985 | Hopp | |
| 6,838,429 | B2 | 1/2005 | Paslin | |
| 2008/0145339 | A1* | 6/2008 | Hermonat | 424/93.2 |
| 2012/0195957 | A1* | 8/2012 | Sachdeva et al. | 424/450 |
| 2013/0231274 | A1* | 9/2013 | Lee et al. | 514/1.7 |

OTHER PUBLICATIONS

Uchida et al., The Journal of Pharmacology and Experimental Therapeutics, 2011, 338(2):443-450.*
Loughran et al., Dermot Walls and Sinéad T. Loughran (eds.), Protein Chromatography: Methods and Protocols, Methods in Molecular Biology, vol. 681, Springer Science+Business Media, LLC, 2011.*
Kang et al., Modified Sod for Cosmeceuticals, IFSCC Conference 2003 Seoul.*
Bos et al.; The 500 Dalton rule for the skin penetration of chemical compounds and drugs; Exp Dermatol.; 9(3):165-169; Jun. 2000.
Briot et al.; Kallikrein 5 induces atopic dermatitis-like lesions through PAR2-mediated thymic stromal lymphopoietin expression in Netherton syndrome; J Exp Med.; 206(5):1135-1147; May 11, 2009.
Cho et al.; Preferential Binding of *Staphylococcus aureus* to Skin Sites of Th2-Mediated Inflammation in a Murine Model; J Invest Dermatol.; 116:658-663, May 2001.
Damon et al.; Broad spectrum chemokine antagonistic activity of a human poxvirus chemokine homolog; Proc Natl Acad Sci U S A.; 26;95(11):6403-6407; May 26, 1998.
Delea et al.; Administrative claims analysis of utilization and costs of care in health plan members with atopic dermatitis who had prior use of a topical corticosteroid and who initiate therapy with pimecrolimus or tacrolimus; J Manag Care Pharm.; 13(4):349-359; May 2007.
Elias et al.; "Outside-to-inside" (and now back to "outside") pathogenic mechanisms in atopic dermatitis; J Invest Dermatol.; 128(5):1067-1070; May 2008.
NCBI RefSeqID: MCU60315; Molluscum contagiosum virus subtype 1, complete genome; http://www.ncbi.nlm.nih.gov/nuccore/U60315.1?report=gbwithparts&log$=seqview; 111pgs.; downloaded Sep. 9, 2013.
NCBI RefSeqID: MCU96749; Molluscum contagiosum virus subtype 2 C—C chemokine-like protein gene, complete cds; http://www.ncbi.nlm.nih.gov/ nuccore/U96749; downloaded Sep. 9, 2013.
Gombert et al.; CCL1-CCR8 interactions: an axis mediating the recruitment of T cells and Langerhans-type dendritic cells to sites of atopic skin inflammation; J Immunol.; 174(8):5082-5091; Apr. 15, 2005.
Griffiths et al.; Therapeutic Potential of Oral L-Histidine in Atopic Dermatitis; J Invest Dermatol.; 132(S2):S51; Aug. 2012.
Haque et al.; Chemokine receptor-8 (CCR8) mediates human vascular smooth muscle cell chemotaxis and metalloproteinase-2 secretion; Blood; 103(4):1296-1304; Feb. 2004.
Hatano et al.; Interleukin-4 suppresses the enhancement of ceramide synthesis and cutaneous permeability barrier functions induced by tumor necrosis factor-alpha and interferon-gamma in human epidermis; J Invest Dermatol.; 124 (4):786-792; Apr. 2005.
Howell et al.; Interleukin-10 downregulates anti-microbial peptide expression in atopic dermatitis; J Invest Dermatol.; 125(4):738-745; Oct. 2005.
Howell et al.; Th2 cytokines act on S100/A11 to downregulate keratinocyte differentiation; J Invest Dermatol.; 128(9):2248-2258; Apr. 2008.
Hussain et al.; DNA, the immune system, and atopic disease; J Investig Dermatol Symp Proc.; 9(1):23-28; Jan. 2004.

(Continued)

*Primary Examiner* — Nicole Kinsey White
(74) *Attorney, Agent, or Firm* — Shay Glenn LLP

(57) ABSTRACT

Compositions, methods, and kits are provided for treating CCR8 mediated diseases with applicability to atopic dermatitis and potential applicability to asthma, prurigo nodularis, nummular dermatitis, neurodermatitis, and lichen simplex chronicus and some lymphomas, multiple sclerosis, acquired immunodeficiency disease, peritoneal adhesions, Kaposi's sarcoma and atherogenesis—the expression of all of which, at least in part, is mediated by cells expressing the chemokine receptor CCR8. The compositions include proteins and fusion proteins from Molluscum contagiosum Virus (MCV) or variants, analogs and derivatives thereof which exhibit inhibitory activity. Examples of such MCV proteins are MC148 fusion protein (MC148fp) identified as MC148P-TAT-6×His ("6×His" disclosed as SEQ ID NO: 11), and its variants, fragments, analogs and derivatives which possess inhibitory activity. The variants, fragments, analogs and derivatives of MC148p and of MC148fp may be less than 100% homologous to MCV proteins as long as they are sufficiently homologous that inhibitory activity is preserved.

11 Claims, 15 Drawing Sheets

(56) References Cited

OTHER PUBLICATIONS

Hvid et al.; IL-25 in Atopic Dermatitis: A Possible Link between Inflammation and Skin Barrier Dysfunction; J Invest Dermatol.; 131:150-157; Jan. 2011.

Ishikawa et al.; Changes in the ceramide profile of atopic dermatitis patients; J Invest Dermatol.; 130(10):2511-2514; Oct. 2010.

Janssens et al.; Lamellar lipid organization and ceramide composition in the stratum corneum of patients with atopic eczema; J Invest Dermatol.; 131(10):2136-2138; Jun. 2011.

Johnson et al.; TAT-mediated delivery of a DNA repair enzyme to skin cells rapidly initiates repair of UV-induced DNA damage; J Invest Dermatol.; 131(3):753-761; Mar. 2011.

Krathwohl et al.; Functional characterization of the C—C chemokine-like molecules encoded by molluscum contagiosum virus types 1 and 2; Proc Natl Acad Sci U S A.; 94(18):9875-9880; Sep. 2, 1997.

Luttichau et al.; A highly selective CC chemokine receptor (CCR)8 antagonist encoded by the poxvirus molluscum contagiosum; J Exp Med.; 191(1):171-180; Jan. 3, 2000.

Macheleidt et al.; Deficiency of epidermal protein-bound omega-hydroxyceramides in atopic dermatitis; J Invest Dermatol.; 119(1):166-173; Jul. 2002.

Nemoto-Hasebe et al.; Clinical Severity Correlates with Impaired Barrier in Filaggrin-Related Eczema; J Invest Dermatol.; 129, 682R689; Sep. 2008.

Shaw et al.; Eczema prevalence in the United States: data from the 2003 National Survey of Children's Health; J Invest Dermatol.; 131(1):67-73; Jan. 2011.

Thakoersing et al.; Increased Presence of Monounsaturated Fatty Acids in the Stratum Corneum of Human Skin Equivalents; J Invest Dermatol.; 133:59-67, Jan. 2013.

Wolf et al.; Topical treatment with liposomes containing T4 endonuclease V protects human skin in vivo from ultraviolet-induced upregulation of interleukin-10 and tumor necrosis factor-alpha; J Invest Dermatol.; 114 (1):149-156; Jan. 2000.

Amann et al.; Effects of IL-31 on skin barrier function and allergen penetration in 3D organotypic skin models; Abstract # 435; J Invest Dermatol; 132:S78; Sep. 2012.

Bieber T., Atopic dermatitis; N Engl J Med.; 358(14):1483-1494; Apr. 3, 2008.

Bugert et al.; Chemokine homolog of molluscum contagiosum virus: sequence conservation and expression; Virology; 242(1):51-59; Mar. 1, 1998.

Da Silva et al.; Abnormal barrier function and allergic skin inflammation in mice overexpressing Th2 cells via a constitutively active Stat6 gene; Abstract # 692; J Invest Dermatol.; 130:S116; Apr. 2010.

Fluhr et al.; Infant epidermal skin physiology: adaptation after birth; Br J Dermatol.; 166(3):483-90; Mar. 2012.

Gittler et al.; Th2 and Th22 mediators initiate and maintain progression of atopic dermatitis; Abstract # 078; J Invest Dermatol.; 132:S13, May 2012.

Gobel et al.; 1,2-pentanediol enhances cutaneous penetration and bioavailability of active ingredients; Abstract # P1615; J Am Acad Dermatol.; 60(3) Suppl. 1:AB82; Mar. 2009.

Higashi et al.; Elevated Serum Levels of I-309/CCL1 in Patients with Severe Atopic Dermatitis; Abstract # OC19; J Invest Dermatol.; 125:601, Sep. 2005.

Irvine et al.; Filaggrin mutations associated with skin and allergic diseases; N Engl J Med.; 365(14):1315-1327; Oct. 6, 2011.

Kyte et al.; A simple method for displaying the hydropathic character of a protein; J Mol Biol.; 157(1):105-132; May 5, 1982.

Mousdicas et al.; *Staphylococcal lipotechoic* acid inhibits delayed type hypersensitivy reactions via the platelet activating factor receptor: A novel mechanism by which *Staphylococcal* infections can worsen atopic derma; Abstract # 157-06; J Am Acad Dermatol.; 52(3)Suppl. 2:AB12; Mar. 2005.

Mousdicas et al.; *Staphylococcal lipotechoic* acid inhibits delayed type hypersensitivy reactions via the platelet activating factor receptor: A novel mechanism by which *Staphylococcal* infections can worsen atopic dermatitis; Abstract # 794; J Am Acad Dermatol.; 122(3):AB133; Mar. 2004.

Morizane et al.; Th2 cytokines enhance tissue kallikreins and serine protease activity of keratinocytes in atopic dermatitis; Abstract # 280; J Invest Dermatol.; 130:S47, Apr. 2010.

Ozkaya E.; Adult-onset atopic dermatitis; J Am Acad Dermatol.; 52 (4):579-582; Apr. 2005.

Senkevich et al.; Genome sequence of a human tumorigenic poxvirus: prediction of specific host response-evasion genes; Science; 273(5276):813-816; Aug. 9, 1996.

Siprashvili et al; Protien delivery to cells and skin tissue via reversible decoration with transporter peptides; Abstract # 303; J Invest Dermatol 122(3): A51, Mar. 2004.

Cornelissen et al.; IL-31 regulates differentiation and filaggrin expression in human organotypic skin models; J Allergy Clin Immunol.; 129(2):426-433 ; Feb. 2012.

Gump et al.; TAT transduction: the molecular mechanism and therapeutic prospects; Trends Mol Med.; 13(10):443-448; Oct. 2007.

* cited by examiner

SEQ. ID. No. 1

MCV Type 1

ORF 148R (166,992 – 167,303)

1   ATGAGGGGCGGAGACGTCTTCGCGAGCGTTGTCTTGATGCTGTTACTTGC

51  ACTACCGCGACCGGGAGTGTCACTCGCGAGACGGAAATGTTGTTTGAATC

101 CCACAAATCGTCCGATCCCGAATCCTTTACTGCAAGATCTATCACGCGTC

151 GACTATCAGGCGATAGGACATGACTGCGGACGGGAAGCTTTCAGAGTGAC

201 GCTGCAAGACGGAAGACAAGGCTGCGTTAGCGTTGGTAACAAGAGCTTAC

251 TAGACTGGCTTCGGGGACACAAGGATCTCTGCCCTCAGATATGGTCCGGG

301 TGCGAGTCTCTGTAA

Figure 1A

SEQ.ID.No.2

MC148R1   Protein

Active      Site

1    MRGGDVFASVVLMLLL . ALPRPGVS . . . . . . . LARRKCCLNPT    35

Hypothetical Receptor
                                           Binding Site

Absent Chemokine
                    Activation Site

36    NRPIPNPLLQDLSRVDYQAIGHDCGREAFRVTLQD    70

71    GRQGCVSVGNKSLLDWLRGHKDLCPQIWSGCESL    104

Figure 1B

SEQ. ID. No. 3

MCV Type 2

ORF 148R (166,992 – 167,303)

1   ATGAGGGCCAGAGCCGTCTTCGCGAGCGTTGTCTTGACGCTGTTACTTGC

51  ACTACCGCGACCGGGAGTGTCACTCTCGAGACGGAAATGTTGTTTGAATC

101 CTACAAATCGTCCGATACCGAGGCCTTTACTGCAAGATCTAGACAAAGTC

151 GATTATCAGCCGATGGGACATGACTGCGGACGGGAAGCTTTCAGAGTGAC

201 GCTGCAAGACGGAAGACAAGGCTGTGTTAGCGTTGGTAACCAGAGTTTAC

251 TAGACTGGCTGAAGGGACACAAGGATCTCTGCCCGCGGATGTGGCCCGGG

301 TGCGAGTCTCTGTAA

Figure 2A

SEQ. ID. No. 4

MC148R2    Protein

Active     Site
                    |          |
1    MRARAVFASVVLTLLL . ALPRPGVS . . . . . . . LSRRKCCLNPT        35
                                 |
                                 | Hypothetical Receptor
                                 | Binding Site
                    Absent Chemokine
                    Activation Site

36   NRPIPRPLLQDLDKVDYQPMGHDCGREAFRVTLQD                          70

71   GRQGCVSVGNQSLLDWLKGHKDLCPRMWPGCESL                           104

Figure 2B

SEQ. ID. No. 5

MCV 148R from Index Case shown for nucleotides 21 to 312
reading in direction from 5' to 3'

| | | |
|---|---|---|
| 21 | CGCGAGCGTTGTCTTGATCCTGTTACTTGCACTACCGCGA | 60 |
| 61 | CCGGGAGTGTCACTCGCGAGACGGAAATGTTGTTTGAATC | 100 |
| 101 | CCACAAATCGTCCGATCCCGAATCCTTTACTGCAAGATCT | 140 |
| 141 | ATCACGCGTCGACTATCAGGCGATAGGACATGACTGCGGA | 180 |
| 181 | CGGGAAGCTTTCAGAGTGACGCTGCAAGACGGAAGACAAG | 220 |
| 221 | GCTGCGTTAGCGTTGGTAACAAGAGCTTACTAGACTGGCT | 260 |
| 261 | TCGGGACACAAGGATCTCTGCCCTCAGATATGGTCCGGG | 300 |
| 301 | TGCGAGTCTCTG | |

Figure 3

SEQ. ID. No. 6

DNA sequence of MCV ORF 148R to which is fused the 33 nucleotides used to produce
the TAT sequence and the 18 nucleotides used to produce the sequence of 6 histidines
at the carboxyl terminal of MCV ORF 148R TAT sequence is underlined
6xHis sequence is italicized

| | |
|---|---|
| 1 | ATGAGGGGCGGAGACGTCTTCGCGAGCGTTGTCTTGATGCTGTTACTTGC |
| 51 | ACTACCGCGACCGGGAGTGTCACTCGTGAGACGGAAATGTTGTTTGAATC |
| 101 | CCACAAATCGTCCGATCCCGAATCCTTTACTGCAAGATCTATCACGCGTC |
| 151 | GACTATCAGGCGATAGGACATGACTGCGGACGGGAAGCTTTCAGAGTGAC |
| 201 | GCTGCAAGACGGAAGACAAGGCTGCGTTAGCGTTGGTAACAAGAGCTTAC |
| 251 | TAGACTGGCTTCGGGGACACAAGGATCTCTGCCCTCAGATATGGTCCGGG |
| 301 | TGCGAGTCTCTG<u>TACGGCAGGAAAAAAGGAGGCAAAGAAGGAGGC</u>*ATCA* |
| 351 | *TCACCATCATCAC* |

Figure 4 A

SEQ. ID. No. 7

The amino acid sequence of the protein produced from the fusion DNA sequence illustrated in FIG. 4 A.

TAT sequence is underlined
6xHis sequence is italicized

Active Site

1 MRGGDVFASVVLMLLL . ALPRPGVS . . . . . . . . LARRKCCLNPT 35

Hypothetical Receptor Binding Site

Absent Chemokine Activation Site

36 NRPIPNPLLQDLSRVDYQAIGHDCGREAFRVTLQD 70

71 GRQGCVSVGNKSLLDWLRGHKDLCPQIWSGCESL 104

105 <u>YGRKKRRQRRR</u>*HHHHHH* 121

Figure 4 B

SEQUENCE LISTING

<160> NUMBER OF SEQ ID NOS: 14

<210> SEQ ID NO 1
<211> LENGTH: 315
<212> TYPE: DNA
<213> ORGANISM: Molluscum contagiosum virus

<400> SEQUENCE: 1

```
atgaggggcg gagacgtctt cgcgagcgtt gtcttgatgc tgttacttgc actaccgcga      60
ccgggagtgt cactcgcgag acggaaatgt tgtttgaatc ccacaaatcg tccgatcccg     120
aatcctttac tgcaagatct atcacgcgtc gactatcagg cgataggaca tgactgcgga     180
cgggaagctt tcagagtgac gctgcaagac ggaagacaag gctgcgttag cgttggtaac     240
aagagcttac tagactggct tcggggacac aaggatctct gccctcagat atggtccggg     300
tgcgagtctc tgtaa                                                      315
```

<210> SEQ ID NO 2
<211> LENGTH: 104
<212> TYPE: PRT
<213> ORGANISM: Molluscum contagiosum virus

<400> SEQUENCE: 2

```
Met Arg Gly Gly Asp Val Phe Ala Ser Val Val Leu Met Leu Leu Leu
1               5                   10                  15

Ala Leu Pro Arg Pro Gly Val Ser Leu Ala Arg Arg Lys Cys Cys Leu
            20                  25                  30
```

Asn Pro Thr Asn Arg Pro Ile Pro Asn Pro Leu Leu Gln Asp Leu Ser
             35                  40                  45

Arg Val Asp Tyr Gln Ala Ile Gly His Asp Cys Gly Arg Glu Ala Phe
 50                  55                  60

Arg Val Thr Leu Gln Asp Gly Arg Gln Gly Cys Val Ser Val Gly Asn
 65                  70                  75                  80

Lys Ser Leu Leu Asp Trp Leu Arg Gly His Lys Asp Leu Cys Pro Gln
             85                  90                  95

Ile Trp Ser Gly Cys Glu Ser Leu
            100

<210> SEQ ID NO 3
<211> LENGTH: 315
<212> TYPE: DNA
<213> ORGANISM: Molluscum contagiosum virus

<400> SEQUENCE: 3
atgagggcca gagccgtctt cgcgagcgtt gtcttgacgc tgttacttgc actaccgcga      60
ccgggagtgt cactctcgag acggaaatgt tgtttgaatc ctacaaatcg tccgataccg     120
aggcctttac tgcaagatct agacaaagtc gattatcagc cgatgggaca tgactgcgga     180
cgggaagctt tcagagtgac gctgcaagac ggaagacaag gctgtgttag cgttggtaac     240
cagagtttac tagactggct gaagggacac aaggatctct gcccgcggat gtggcccggg     300
tgcgagtctc tgtaa                                                      315

<210> SEQ ID NO 4
<211> LENGTH: 104
<212> TYPE: PRT
<213> ORGANISM: Molluscum contagiosum virus

<400> SEQUENCE: 4

Met Arg Ala Arg Ala Val Phe Ala Ser Val Val Leu Thr Leu Leu Leu
 1               5                  10                  15

Ala Leu Pro Arg Pro Gly Val Ser Leu Ser Arg Arg Lys Cys Cys Leu
             20                  25                  30

Asn Pro Thr Asn Arg Pro Ile Pro Arg Pro Leu Leu Gln Asp Leu Asp
             35                  40                  45

Lys Val Asp Tyr Gln Pro Met Gly His Asp Cys Gly Arg Glu Ala Phe
 50                  55                  60

Arg Val Thr Leu Gln Asp Gly Arg Gln Gly Cys Val Ser Val Gly Asn
 65                  70                  75                  80

Gln Ser Leu Leu Asp Trp Leu Lys Gly His Lys Asp Leu Cys Pro Arg
             85                  90                  95

Met Trp Pro Gly Cys Glu Ser Leu
            100

<210> SEQ ID NO 5
<211> LENGTH: 292
<212> TYPE: DNA
<213> ORGANISM: Molluscum contagiosum virus

<400> SEQUENCE: 5
cgcgagcgtt gtcttgatgc tgttacttgc actaccgcga ccgggagtgt cactcgcgag      60
acggaaatgt tgtttgaatc ccacaaatcg tccgatcccg aatcctttac tgcaagatct     120
atcacgcgtc gactatcagg cgataggaca tgactgcgga cgggaagctt tcagagtgac     180
gctgcaagac ggaagacaag gctgcgttag cgttggtaac aagagcttac tagactggct     240
tcggggacac aaggatctct gccctcagat atggtccggg tgcgagtctc tg    292

<210> SEQ ID NO 6
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6
atgaggggcg agacgtctt cgcgagcgtt gtcttgatgc tgttacttgc actaccgcga    60
ccgggagtgt cactcgtgag acggaaatgt tgtttgaatc ccacaaatcg tccgatcccg    120
aatcctttac tgcaagatct atcacgcgtc gactatcagg cgataggaca tgactgcgga    180
cgggaagctt tcagagtgac gctgcaagac ggaagacaag gctgcgttag cgttggtaac    240
aagagcttac tagactggct tcggggacac aaggatctct gccctcagat atggtccggg    300
tgcgagtctc tgtacggcag gaaaaaaagg aggcaaagaa ggaggcatca tcaccatcat    360
cac    363

<210> SEQ ID NO 7
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Arg Gly Gly Asp Val Phe Ala Ser Val Val Leu Met Leu Leu Leu
1               5                   10                  15

Ala Leu Pro Arg Pro Gly Val Ser Leu Ala Arg Arg Lys Cys Cys Leu
            20                  25                  30

Asn Pro Thr Asn Arg Pro Ile Pro Asn Pro Leu Leu Gln Asp Leu Ser
        35                  40                  45

Arg Val Asp Tyr Gln Ala Ile Gly His Asp Cys Gly Arg Glu Ala Phe
    50                  55                  60

Arg Val Thr Leu Gln Asp Gly Arg Gln Gly Cys Val Ser Val Gly Asn
65                  70                  75                  80

Lys Ser Leu Leu Asp Trp Leu Arg Gly His Lys Asp Leu Cys Pro Gln
                85                  90                  95

Ile Trp Ser Gly Cys Glu Ser Leu Tyr Gly Arg Lys Lys Arg Arg Gln
            100                 105                 110

Arg Arg Arg His His His His His
        115                 120

<210> SEQ ID NO 8
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This sequence may encompass 3-20 residues

<400> SEQUENCE: 8

His His His His His His His His His His His His His His His

```
1               5                   10                  15
His His His His
                20

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: This sequence may encompass 4-12 residues

<400> SEQUENCE: 9

His His His His His His His His His His His His
1               5                   10

<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(8)
<223> OTHER INFORMATION: This sequence may encompass 5-8 residues

<400> SEQUENCE: 10

His His His His His His His His
1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 11

His His His His His His
1               5

<210> SEQ ID NO 12
<211> LENGTH: 11
<212> TYPE: PRT
<213> ORGANISM: Human immunodeficiency virus

<400> SEQUENCE: 12

Tyr Gly Arg Lys Lys Arg Arg Gln Arg Arg Arg
1               5                   10

<210> SEQ ID NO 13
<211> LENGTH: 10
<212> TYPE: PRT
<213> ORGANISM: Molluscum contagiosum virus

<400> SEQUENCE: 13

Val Ser Leu Ala Arg Arg Lys Cys Cys Leu
1               5                   10

<210> SEQ ID NO 14
```

```
<211> LENGTH: 20
<212> TYPE: PRT
<213> ORGANISM: Molluscum contagiosum virus

<400> SEQUENCE: 14

Pro Arg Pro Gly Val Ser Leu Ala Arg Arg Lys Cys Cys Leu Asn Pro
1               5                   10                  15

Thr Asn Arg Pro
            20
```

VIRAL FUSION PROTEIN TREATMENT FOR CCR8 MEDIATED DISEASES

CROSS REFERENCE TO RELATED APPLICATIONS

None.

SEQUENCE LISTING

The instant application contains a Sequence Listing which has been submitted in ASCII format via EFS-Web and is hereby incorporated by reference in its entirety. Said ASCII copy, created on Jul. 31, 2013, is named 12744-700_200_SL_txt and is 7,483 bytes in size.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates to the treatment of disorders of skin and of other organs, more particularly atopic dermatitis, mediated by chemokine receptor CCR8, using compositions which include a protein derived from Molluscum contagiosum Virus (MCV).

BACKGROUND

Atopic dermatitis (AD) is a genetically determined, reaginically (IgE) associated, chronic disease of the skin in which the skin is dry, easily irritated, allergen predisposed, typically scaly, often thickened, commonly red, sometimes exudative, frequently infected and above all itchy. In the United States prevalence rates in childhood range from 8.7 to 18.1% with higher rates in metropolitan areas and among the more affluent. (J Invest Dermatol 131:67-73, 2011). AD may persist into or reappear in adulthood, but may also arise in adult life. (J Am Acad Dermatol 52:579-82, 2005). In industrialized countries, the prevalence rates in childhood range from 15 to 30% and in adults from 2 to 10% of the general population. (NEJM 358:1483-94, 2008). AD adversely affects the quality of life of the patients and their families and imposes a significant financial burden measured in billions of dollars (J Manag Care Pharm 13:349-59, 2007).

Atopic dermatitis is characterized both by a defective skin barrier, the stratum corneum, and by a defective immune response, characterized by Th2 dominance. In the former case, disease pathogenesis follows an outside-to-inside pathway and in the latter case, disease pathogenesis follows an inside-to-outside pathway. (J Invest Dermatol 128:1067-1070, 2008).

Pursuant to outside-to-inside pathogenesis, there are 2 main attributes of the defective skin barrier. One of these attributes results from a deficiency in ceramides, the main lipid in the stratum corneum. Ceramide deficiency characterizes patients with AD, noting that ceramides consist of a union between long chain fatty acids (FA) and sphingosine (S) bases. There is a significant reduction in esterified omega-OH-FA and sphingosine base (EOS), in esterified omega-OH-FA and 6-OH-sphingosine base (EOH), in esterified omega-OH-FA and phytosphingosine base (EOP), in non-OH-FA and 6-OH-sphingosine base (NH), and in non-OH-FA and phytosphingosine base (NP). (J Invest Dermatol 130:2511-14, 2010). The esterified omega-OH-ceramides exist in free and in bound forms—the latter being bound to proteins of the keratinocytic cornified envelope, mostly involucrin. In non-lesional and yet more in lesional skin of patients with AD, there is a marked reduction of these esterified ceramides bound to the cornified envelope. Similarly there is a marked reduction of free extractable very long chain FA, i.e. >24 carbon atoms, both in non-lesional and more severely in lesional skin of patients with AD. These defects contribute to the barrier impairment seen in AD. (J Invest Dermatol 119:166-73, 2002). These changes in ceramide composition are associated with a change in the lamellar lipid organization in AD patients. (J Invest Dermatol 131:2136-38, 2011).

The other main attribute results from genetically induced deficiency in filaggrin, a histidine rich protein whose diminution is found in about ⅓ of patients with AD and in whom clinical severity correlates with transepidermal water loss (TEWL) and poor stratum corneum hydration, whereas similar correlation does not pertain in patients lacking filaggrin deficiency. (J Invest Dermatol 129:682-89, 2008). Yet barrier abnormalities remain in patients with AD lacking filaggrin deficiency, further noting that filaggrin deficiency alone is not sufficient to generate AD as in patients with ichthyosis vulgaris. Nonetheless AD patients with filaggrin mutations have reduced hydroscopic amino acids as well as reduced tight junctions and reduced corneodesmosin, yielding defective intercorneocyte adhesion. These patients manifest persistent disease, a higher incidence of eczema herpeticum, irritant contact dermatitis, allergic contact dermatitis, peanut allergy and asthma. (NEJM 365:1315-27, 2011). Further, filaggrin breakdown products include polycarboxylic acids—the lack of which increases stratum corneum pH, which in turn activates serine proteases. These proteases appear to induce corneocytes to release IL-1α and IL-1β from their pro-forms, initiating inflammatory pathways. These proteases may also mediate Th2 inflammation, even in the absence of allergen priming. (J Exp Med 206:1135-47, 2009).

Pursuant to inside-to-outside pathogenesis, Th2 cytokines may impair the skin barrier. Th2 cytokines include IL-4, IL-5, IL-6, IL-10 and IL-13 (J Invest Dermatol Symp Proc 9:23-8, 2004). Among these cytokines, it has been shown that IL-4 not only inhibits ceramide synthesis in cultured keratinocytes (J Invest Dermatol 124:786-92, 2005) but also inhibits epidermal differentiation complex genes, resulting in significantly lower levels of filaggrin, loricrin and involucrin (J Invest Dermatol 130:S116, 2010). Indeed both Th2 cytokines IL-4 and IL-13 inhibit both filaggrin and human β-defensin 3 expression. (J Invest Dermatol 128: 2248-58, 2008). IL-22 is found in AD skin. It, too, down regulates filaggrin expression in keratinocytes. IL-10 down regulates anti-microbial peptide expression in AD (J Invest Dermato 125:738-45, 2005). IL-31, highly expressed in skin samples of AD patients and associated with the itching of AD, inhibits the expression of terminal differentiation markers including filaggrin (J All Clin Immunol 129:426-33, 2012). Further IL-31 treated skin models resulted in increased uptake of allergens of timothy grass and cat dander, demonstrating increased transepidermal penetration of environmental allergens (J Invest Dermatol 132: S78, 2012).

Dendrocytes are increased in number in AD skin and produce IL-25 (IL-17E). IL-25 levels are elevated in the skin of AD patients and it induces and prolongs Th2 immune responses. Specifically, IL-25 induces production of IL-4, IL-5, IL-13, IgE and eosinophilia in a murine model of asthma. In addition to this, IL-25 decreases synthesis of filaggrin in cultured keratinocytes (J Invest Dermatol 131:150-7, 2011). Kallikrein, including kallikrein 7, are serine proteases, elevated in the epidermis of AD patients. Overexpression of human kallikrein 7 in murine epidermis results in a chronic itchy dermatitis. Cultured normal human epidermal keratinocytes treated with IL-4 or IL-13 increased kallikrein levels. Kallikreins 1, 8, 11, 12 and 13 were similarly induced (J Invest Dermatol 130:S47, 2010). Kallikreins elevate tissue pH which impairs glucocerebrosidase and sphingomyelinase—both of which require acidic pH, resulting in impaired ceramide production and impairment of the skin barrier.

It has been shown that Th2 cytokines and Th22 cytokines remain dominant in acute and chronic phases of AD. A claim that acute AD is followed by chronic AD is somewhat of a mischaracterization because AD is almost always a chronic dermatitis in which the patient clinically experiences (acute) flares of AD. Irrespective of such characterization, Th2 cytokines, including IL-4 and IL-10, as well as Th22 cytokines, IL-22 and IL-31, are up regulated in "acute" AD and are increased even more in "chronic" AD such that Th2 and Th22 cytokines are dominant throughout the disease course (J Invest Dermatol 132:S13, 2012).

The frequent chronic infections that occur on and in the skin of AD patients appear to result both from the defective skin barrier of AD and from an impaired immune response, e.g. upon testing with *trichophyton* antigen, patients with AD show immediate rather than the normal delayed immune response. The most common of the microbes infecting AD skin is *Staphylococcus aureus* (Staph). In AD skin, Staph induces and exacerbates itching, increases inflammation and provokes oozing and eczematization. Of patients whose skin oozes, 100% will culture out Staph. Of those who do not ooze, the majority will still culture out Staph, although less massively. Staph binds readily to Th2 inflamed skin as compared with Th1 inflamed skin, perhaps accounting for the high colonization rate of AD skin (J Invest Dermatol 116:658-63, 2001).

Staph contributes to AD disease expression. Lipoteichoic acid is a constituent of the cell wall of Staph. It is a potent agonist of platelet-activating factor receptor (PAF-R). Lipoteichoic acid and PAF-R suppress Th1 type reactions but up-regulate production of IL-10, a Th2 cytokine (J Am Acad Dermatol AB12, March 2005), contributing to the Th2 dominant inflammation of AD. Further IL-10 is elevated in both extrinsic and intrinsic forms of AD. IL-10 inhibits the expression of antimicrobial peptides, enabling Staph colonization (J Invest Dermatol 125:738-745, 2005). Staph derived ceramidase may aggravate the skin barrier defect of AD. Staph enterotoxins inhibit the suppressive activity of regulatory T cells and correlate with AD severity. Staph exotoxins up-regulate Th22 cell production of the highly pruritogenic IL-31. About 50% of patients with AD produce IgE directed against Staph toxins and IgE is a chief mediator of Th2 inflammation.

Viruses, too, more readily grow in AD skin than in normal skin. Viruses commonly colonizing AD skin include herpes simplex, *verruca vulgaris* and molluscum contagiosum.

There is no known cure for AD. The many treatment approaches attest the inadequacy and limitations of each. In briefest outline, these treatments include avoidance of soap, irritants and allergens, hydration of the skin, dietary restrictions, tars, antihistamines, hyposensitization, corticosteroids, antibacterials, antifungals, antivirals, ultraviolet light, leukotriene blockers, inhibitors of mast cell content release, evening primrose oil, Chinese herbal teas, pentoxifylline, pimecrolimus, tacrolimus, azathioprine, cyclosporin A, cyclophosphamide, interferon γ, thymopentin and phosphodiesterase inhibitors. The corticosteroids are most commonly used in clinical practice, but suffer from incomplete responses, tachyphylaxis, induction of atrophy and the potential of suppression of the pituitary-adrenal axis if used widely enough, long enough and potently enough.

SUMMARY OF THE DISCLOSURE

The present disclosure relates to compositions, methods and kits for treating atopic dermatitis, other atopic diseases, including asthma, allergic rhinitis, hives, other Th2 mediated diseases and diseases mediated by the CC chemokine receptor, CCR8. Compositions, methods, and kits are provided for treating CCR8 mediated diseases with applicability to atopic dermatitis and potential applicability to asthma, prurigo nodularis, nummular dermatitis, neurodermatitis, and lichen simplex chronicus as well as some lymphomas, multiple sclerosis, acquired immunodeficiency disease, peritoneal adhesions, Kaposi's sarcoma and atherogenesis—the expression of all of which, at least in part, is mediated by cells expressing the chemokine receptor CCR8. The compositions according to the present disclosure include proteins from Molluscum Contagiosum Virus (MCV), short or long peptide sequences fused to MCV proteins, or fragments, variants, analogs, and derivatives thereof which exhibit AD and CCR8 inhibiting activity plus the capacity to penetrate intact human skin as well as exhibiting the inhibition of chemotaxis and/or function of cells expressing CCR8, including Th2 cells, monocytes, macrophages, dendrocytes, Langerhans cells, natural killer cells, endothelial cells, and smooth muscle cells (Blood 103:1296-1304, 2004). Examples of MCV proteins which exhibit AD inhibiting activity plus the capacity to penetrate intact human skin as well as exhibiting the inhibition of chemotaxis and/or function of cells expressing CCR8, include MC148p1 (Molluscum Contagiosum 148 protein—being the product of type 1 MCV gene/open reading frame 148, reading right), MC148p2, MC148p3, MC148fp (Molluscum Contagiosum 148 protein fused with one or more than one short peptide sequence and/or with one or more than one long peptide sequence, variants, analogs and derivatives thereof which exhibit AD inhibiting activity, human skin penetrating capacity and/or exhibiting the inhibition of chemotaxis and/or function of cells expressing CCR8 and other MC148p and MC148fp types of proteins which possess AD inhibiting and/or human skin penetrating capacity as well as exhibiting inhibition of cells expressing CCR8. Such a short or long peptide sequence fused with Molluscum Contagiosum 148 protein may be a TAT sequence (such as described herein). Such a TAT sequence may be fused to the N-terminus of the Molluscum Contagiosum 148 protein, may be fused to the C-terminus of the Molluscum Contagiosum 148 protein, or may be placed in the middle of the Molluscum Contagiosum 148 protein. In some embodiments, a TAT sequence may be separated from the Molluscum Contagiosum 148 protein on the N-terminus or on the C-terminus by another peptide, such as a spacer or another domain-containing peptide. Such a short or long peptide sequence fused with Molluscum Contagiosum 148 protein may be a polyHis peptide. A polyHis peptide may include, for example, from 3-20 histidine residues (SEQ ID NO: 8), from 4-12 histidine residues (SEQ ID NO: 9), from 5-8 histidine residues (SEQ ID NO: 10), or may include 6 histidine residues ("6×His") (SEQ ID NO: 11). In some embodiments, such a polyHis sequence may be separated from the Molluscum Contagiosum 148 protein on the N-terminus or on the C-terminus by another peptide, such as a spacer or another domain-containing peptide. In some embodiments, such a polyHis sequence may be in the middle of a Molluscum Contagiosum 148 protein. In some embodiments, an MC148 fusion protein (MC148fp) includes a Molluscum Contagiosum 148 protein with a TAT sequence fused to its C-terminal end and a 6×His (SEQ ID NO: 11) sequence fused to the TAT sequence (MC148p-C-TAT-6×His ("6×His" disclosed as SEQ ID NO: 11)). In some embodiments, an MC148 fusion protein (MC148fp) includes a Molluscum Contagiosum 148 protein with a TAT sequence at its C-terminal end and a 6×His (SEQ ID NO: 11) sequence located C-terminal to the TAT sequence with a spacer or another peptide (e.g. a domain peptide) separating the MC148 from the TAT and/or from the 6×His (SEQ ID NO: 11).

The fragments, variants, analogs, derivatives and fusions may be less than 100% homologous to MC148p1, MC148p2, MC148p3 as well as MC148fp1, MC148fp2, MC148fp3 so long as they are sufficiently homologous such that AD inhibiting activity and/or human skin penetrating capacity and/or exhibiting inhibition of chemotaxis or function of cells expressing CCR8 are preserved. Collectively, the above MCV proteins, fusions proteins, fragments, variants, analogs and derivatives are referred to herein as MC148 proteins (MC148p) and MC148 fusion proteins (MC148fp).

In one embodiment, the composition is suitable for topical application to a portion of patient's skin which exhibits AD signs and/or symptoms. In another embodiment, the composition is adapted for delivery by other routes including by injection intravenously, intramuscularly, subcutaneously or intradermally or by electroporation or iontophoresis. The composition may be delivered systemically to treat Th2 mediated diseases or to treat CCR8 mediated diseases or it may be delivered remotely or locally at or near a portion of patient's skin which exhibits AD signs and/or symptoms or related skin or non-skin inflammatory diseases.

The disclosure also relates to a kit which includes a composition according to the present disclosure. The kit may optionally include multiple separately packaged portions of the composition, where each portion is in an amount suitable for a single administration or for multiple administrations, e.g. administration from an intravenous line, a syringe, a bottle, a tube or a jar. The kit may also optionally include instructions regarding the administration of the composition to a patient having AD, other atopic diseases, other inflammatory disorders, Th2 mediated diseases or CCR8 mediated diseases. In one of the many variations, the instructions may teach how to administer the composition systemically or locally to the patient.

One aspect of the invention provides a method for treating a patient having at least one of atopic dermatitis, an atopic dermatitis-related atopic disease, an allergic disease, a Th2 mediated disorder and a CCR8 mediated disorder, including the steps of administering to a patient having at least one of atopic dermatitis, an atopic dermatitis-related atopic disease, an allergic disease, a Th2 mediated disorder or a CCR8 mediated disorder, a therapeutically effective amount of a composition comprising a Molluscum contagiosum viral fusion protein MC148p-TAT-poly-His(MC148fp) which possesses at least one of atopic dermatitis inhibitory activity, an atopic dermatitis-related atopic disease inhibitory activity, an allergic disease inhibitory activity, a Th2 mediated disorder inhibitory activity or a CCR8 mediated disorder inhibitory activity. In some embodiments, administering to a patient includes administering an MC148fp selected from the group consisting of Molluscum contagiosum viral fusion protein 148fp1 (MC148fp1), Molluscum contagiosum viral fusion protein 148fp2 (MC148fp2), Molluscum contagiosum viral fusion protein 3 (MC148fp3) and a fragment, a variant, an analog and a derivative of these compositions, fused with C-terminal TAT and poly-His. In some such embodiments, the method includes administering an MC148fp selected from the group consisting of Molluscum contagiosum viral fusion protein 148fp1 (MC148fp1), Molluscum contagiosum viral fusion protein 148fp2 (MC148fp2), Molluscum contagiosum viral fusion protein 3 (MC148fp3) and a fragment, a variant, an analog and a derivative of these compositions, fused at its C-terminus with TAT wherein the TAT is fused with 6×His (SEQ ID NO: 11).

In some embodiments, the method of administering the composition includes topically applying the composition. In some embodiments, the method of administering the composition includes injecting the composition into the patient. In some embodiments, the method of administering the composition includes performing iontophoresis. In some embodiments, the method of administering the composition includes electroporating the composition. In some embodiments, the method of administering the composition includes administering a liposomal carrier to the patient. In some embodiments, the method of administering the composition includes administering a skin penetration enhancement carrier. In some embodiments, the method of administering the composition includes administering nanoparticles, such as, e.g. alginate-chitosan nanoparticles. In some embodiments, the method of administering the composition includes delivering the composition locally to an area of patient skin affected with at least one of atopic dermatitis, an atopic dermatitis-related atopic diseases, an allergic disease, a Th2 mediated disorder and/or a CCR8 mediated disorder. In some embodiments, the method of administering the composition includes delivering the composition to an area of patient skin lacking atopic dermatitis, an atopic dermatitis-related atopic diseases, an allergic disease, a Th2 mediated disorder and a CCR8 mediated disorder. In some embodiments, the method of delivering the composition further includes penetration of the composition through a stratum corneum of the patient.

Another aspect of the invention provides a kit for treating at least one of atopic dermatitis, an atopic dermatitis-related atopic diseases, an allergic disease, a Th2 mediated disorder or a CCR8 mediated disorder, including: multiple separately packaged portions of a composition adapted for such treatment comprising a therapeutically effective amount of a composition comprising a Molluscum contagiosum viral fusion protein MC148p-TAT-polyHis (MC148fp) which possesses at least one of atopic dermatitis inhibitory activity, an atopic dermatitis-related atopic disease inhibitory activity, an allergic disease inhibitory activity, a Th2 mediated disorder inhibitory activity and a CCR8 mediated disorder inhibitory activity.

In some embodiments, the MC148fp is selected from the group consisting of Molluscum contagiosum viral fusion protein 148fp1 (MC148fp1), Molluscum contagiosum viral fusion protein 148fp2 (MC148fp2), Molluscum contagiosum viral fusion protein 3 (MC148fp3) and a fragment, a variant, an analog and a derivative of these compositions, fused with C-terminal TAT and polyHis in either order and with or without spacer peptides. In some embodiments, the MC148fp is selected from the group consisting of Molluscum contagiosum viral fusion protein 148fp1 (MC148fp1), Molluscum contagiosum viral fusion protein 148fp2 (MC148fp2), Molluscum contagiosum viral fusion protein 3 (MC148fp3) and a fragment, a variant, an analog and a derivative of these compositions, fused with C-terminal TAT and 6×His (SEQ ID NO: 11) wherein the 6×His (SEQ ID NO: 11) is C-terminal to the TAT.

In some embodiments, the kit further includes instructions teaching administration of the composition to a patient having at least one of the above-mentioned ailments. In some such embodiments, the instructions teach local delivery of the composition to a patient skin area having, adjacent to, or distant from at least one of the above-mentioned ailments. In some embodiments, the instructions teach topical application of the composition. In some embodiments, the instructions teach injection of the composition. In some embodiments, the instructions teach administering the composition through iontophoresis. In some embodiments, the instructions teach administering the composition through electroporation. In some embodiments, the instructions teach administering a composition that includes a liposomal carrier. In some embodiments, the instructions teach administering a composition that includes a skin penetration enhancer. In some embodiments, the instructions teach administering a composition that includes nanoparticles, such as e.g., alginate-chitosan nanoparticles.

Another aspect of the invention provides a composition including a Molluscum contagiosum viral fusion protein (MC148p-TAT-polyHis) which possesses atopic dermatitis inhibiting activity.

In some embodiments, the composition includes Molluscum contagiosum viral fusion protein (MC148p-TAT-6×His ("6×His" disclosed as SEQ ID NO: 11)) which possesses atopic dermatitis inhibiting activity. In some embodiments, the composition further comprises PBS or other vehicles such as creams, lotions or gels, including hydrogels or occlusion techniques.

In some embodiments, the composition includes a pharmaceutically acceptable carrier. In some embodiments, the composition includes a skin penetration enhancer. In some embodiments, the composition includes dimethylsulfoxide. In some embodiments, the composition includes a liposomal carrier with or without a hydrogel. In some embodiments, the composition includes nanoparticles, such as, e.g., alginate-chitosan nanoparticles.

In some embodiments, the MC148p-TAT-polyHis is selected from the group consisting of: MC148fp1, MC148fp2, and MC148fp3.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A illustrates the DNA sequence (SEQ. ID. No. 1) of MCV type 1, ORF 148 R.

FIG. 1B illustrates the amino acid sequence (SEQ. ID. No. 2) of the protein produced from the DNA sequence of MCV type 1, ORF 148 R, illustrated in FIG. 1A.

FIG. 2A illustrates the DNA sequence (SEQ. ID. No. 3) of MCV type 2, ORF 148 R.

FIG. 2B illustrates the amino acid sequence (SEQ. ID. No. 4) of the protein produced from the DNA sequence of MCV type 2, ORF 148 R, illustrated in FIG. 2A.

FIG. 3 illustrates the DNA sequence (SEQ. ID. No. 5) of MCV ORF 148 R from the index case—the DNA of which is identical to that of MCV type 1, ORF 148 R, shown for nucleotides 21-312.

FIG. 4A illustrates the DNA sequence (SEQ. ID. No. 6) of MCV ORF 148 R to which is fused the 33 nucleotides used to produce the TAT sequence and the 18 nucleotides used to produce the sequence of 6 histidines (SEQ ID NO: 11) at the carboxyl terminal of MCV ORF 148 R.

FIG. 4B illustrates the amino acid sequence (SEQ. ID. No. 7) of the protein produced from the fusion DNA sequence illustrated in FIG. 4A. FIG. 4B discloses "6×His" as SEQ ID NO: 11.

FIG. 8B discloses "6His" as SEQ ID NO: 11.

DETAILED DESCRIPTION

Atopic dermatitis remains a vexing problem for the multitude of individuals suffering with it. Better methods and compositions for treating it are warranted. The compositions of the present disclosure include MC148 proteins and fusion proteins which exhibit AD inhibiting activity and/or human skin penetration capacity and/or inhibition of chemotaxis and/or function of cells expressing CCR8. As noted above, these proteins may be MCV proteins or MCV fusion proteins such as MC148p1, MC148p2, MC148p3, MC148fp1, MC148fp2, MC148fp3 as well as other fusions, fragments, variants, analogs, and derivatives of the MCV proteins, including those described in U.S. Pat. No. 6,838,429 to David A. Paslin, which exhibit AD inhibiting activity and/or human skin penetration capacity and/or inhibition of chemotaxis and/or function of cells expressing CCR8. The fusions, fragments, variants, analogs and derivatives may be less than 100% homologous to a MCV protein so long as they are sufficiently homologous such that AD inhibiting activity and/or human skin penetration activity and/or inhibition of chemotaxis and/or inhibition of function of cells expressing CCR8 are preserved.

Molluscum Contagiosum Virus (MCV) is a large 190 kDa DNA virus of the Pox family. MCV causes small, harmless lesions in the skin of infected persons. These small papules (bumps) resemble pimples that typically appear domed, shiny and often show a small central invagination (pit). MCV can be spread from person to person by direct skin contact and by fomites. It is harmless, non-invasive and has no cancerous potential. MC148p1 is natively produced by MCV type 1. MC148p2 is natively produced by MCV type 2.

The Applicant has observed in his clinical practice of medicine the inhibitory effect of MCV upon AD. The inhibitory effect endured at least 6 years, i.e. for the duration of the MCV infection, without any clinical side effect and without tachyphylaxis. By viewing macro-lens photographs at focal distances of 15 cm (FIG. 5A) and of 5 cm (FIG. 5B) one sees a field of AD manifest as mildly scaly, somewhat lichenified reddish brown skin. Clear zones of clinically normal skin surround each papule of MCV. The zone of inhibition around each MCV papule may be viewed as analogous to the zone of inhibition around a penicillin disk on an agar plate streaked with Streptococci. The therapeutic implications are also analogous.

Figure 6A:
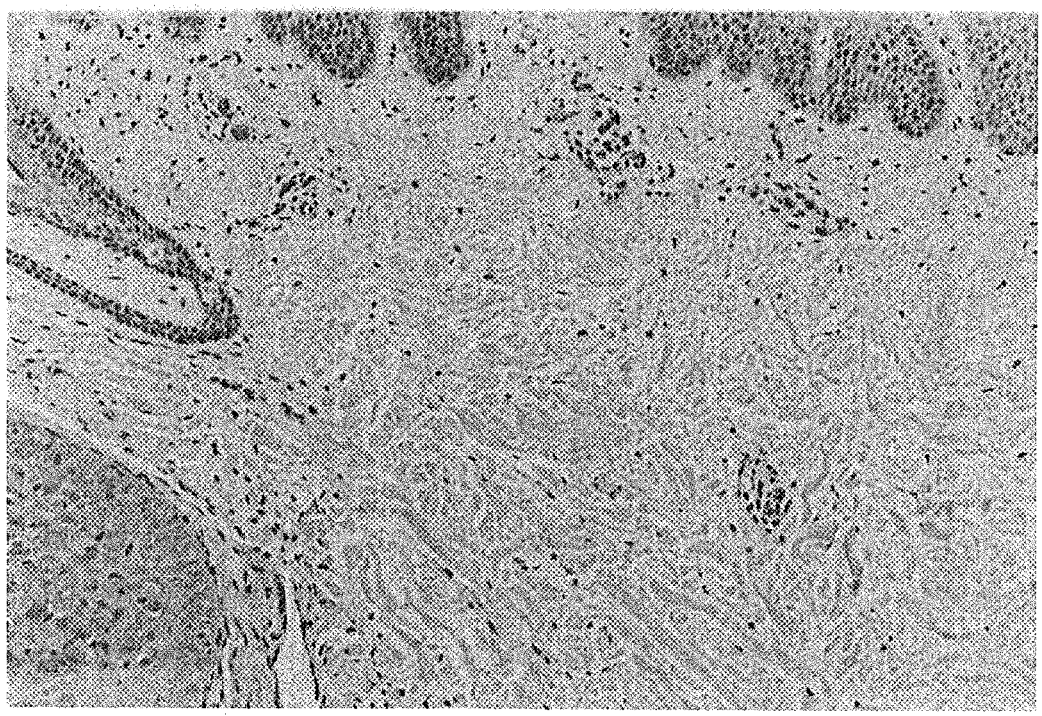
FIG. 6A illustrates the microscopically demonstrable inhibitory effect of MCV upon a field of AD.
Figure 6B:
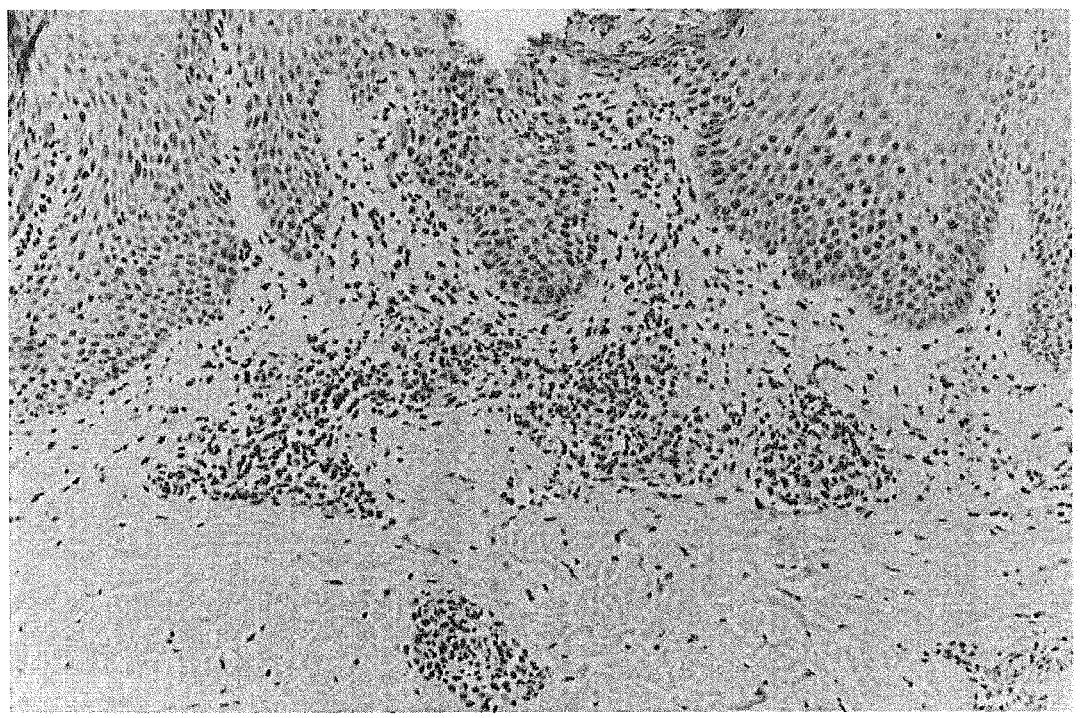
FIG. 6B illustrates the appearance of AD in the same patient shown in FIG. 5A at the same time at a site of AD remote from MCV.

FIG. 6A shows a photomicrograph of a biopsy taken at the edge of and immediately adjacent to a papule of MCV. The edge of the papule is seen at the lower left of the panel. The top of the panel shows the base of the epidermis. A paucity of mononuclear cells is accompanied by a paucity of small blood vessels in the dermis adjacent to the MCV papule. The lack of inflammation in the dermis adjacent to the MCV papule resembles the appearance of the dermis in normal, i.e. non-AD skin. By contrast, FIG. 6B shows a photomicrograph of a biopsy taken concurrently from a similar area of AD on the same patient, but remote from any MCV papule. The moderately dense, predominantly lymphohistiocytic/dendrocytic infiltrate admixed with eosinophils is seen not only around the blood vessels of the superficial plexus, but also around vessels of the papillae and those of the upper reticular dermis. The inflammatory cells extend into the interstitium.

The Applicant interprets the above observations to show that MCV produces a protein that inhibits the signs and symptoms of AD. This protein is believed to be MC148p1. Published work indicates that MC148p2 and other MC148 proteins share the same or similar anti-inflammatory properties. (Krathwohl M D et al. in Proc Nat'l Acad Sci 94:9875-98801997; Bugert J J et al. in Virology 242:51-59, 1998; Damon I et al. in Proc Nat'l Aca Sci 95-6403-6407, 1998.)

MCV type 1 is the major type of MCV found in nature and has of 190,289 base pairs. This comprises the entire genome, excepting covalently closed terminal hairpin loops. This genome was deposited in Gen Bank (accession number U60315) as described by Senkevich TG "Genome Sequence of a Human Tumorigenic Poxvirus: Prediction of Specific Host Response-Evasion Genes" in Science 273:813-816, 1996. MCV type 1 includes a DNA sequence of 312 base pairs, identified as ORF 148 R, that encode a protein of 104 amino acids in length referred to herein as MC148p1. Synthesis, characterization and effects of MC148p1 are discussed in Damon I et al. "Broad Spectrum Chemokine Antagonistic Activity of a Human Poxvirus Chemokine Homolog" Proc Nat'l Acad Sci USA 95:6403-6407, 1998 and in Krathwohl M D et al. "Functional Characterization of the C-C Chemokine-like Molecules Encoded by Molluscum Contagiosum Virus Types 1 and 2" Proc Natl Acad Sci USA 94:9875-9880, 1997.

The DNA sequence of MCV 148 type 1 (SEQ ID No. 1) is illustrated in FIG. 1A and the amino acid sequence of MC148p1 is provided in FIG. 1B. MC148p2 (also denoted MC148R 2 Protein), produced by MCV type 2, is a variant of MC148p1. MC148p2 is also 104 amino acids in length. The DNA sequence for MCV type 2 (SEQ ID No. 3) is illustrated in FIG. 2A and the amino acid sequence of MC148p2 (SEQ ID No. 4) is illustrated in FIG. 2B. The DNA sequence for MC148R2 has been deposited in Gen Bank (Accession number U96749) by Krathwohl et al., as referenced above.

MC148R2 has 89% homology to MC148R1. Amino acid sequences of MC148R2 protein (MC148p2) showed 87% homology with those of MC148p1 for complete sequences and 86% homology when the putative leader sequence was removed. From the amino terminus, the leader sequences of MC148p1 and MC148p2 consist of 24 amino acids of which 20 amino acids share identical positions. The chemokine activation domain, found between positions 24 and 25 of MC148p1 and MC148p2 is absent in both. The 5 amino acids of positions 25-29, comprising the hypothetical receptor binding site, are identical except at position 26 where MC148p2 bears a serine substitution for the alanine residue found in most isolates of MC148p1. This substitution at position 26 does not appear to affect the inhibitory activity of either type of MC148p. The leucine at position 47 from the amino terminus, correlated with the ability of MC148p to inhibit neutrophil chemotaxis, is conserved in MC148p1 and MC148p2.

Further, the amino acid sequences of MC and MC148p2 share significant homology with CC (β) chemokines such as macrophage inflammatory protein-1α (MIP-1α) and MIP-1β (Krathwohl et. see above) and CC (β) chemokines including RANTES, macrophage chemotactic proteins-1 and -3 (MCP-1 and MCP-3) (Damon et al., see above). The amino acid sequences of MC148p1 and of MC148p2 also share significant homology with CXC (α) chemokines SDF-1 for the attraction of monocytes and lymphocytes and IL-8 for the attraction of neutrophils. MC148p1 and MC148p2 share the identical positions of the 4 canonical cysteine residues with the above mentioned CC chemokines at positions 30, 31, 59 and 75 of the respective amino acid chains. Taken together, these structural homologies may best account for the capacity of MC148p to inhibit the chemotaxis of human peripheral blood mononuclear cells (Krathwohl et al.) and of monocytes, lymphocytes and neutrophils (Damn et al.). The inhibition results from the direct binding of MC148p to chemokine receptor(s). It is emphasized, however, that Luttichau et al. in contrast with Damon et al. did not find "promiscuous" inhibition of multiple receptors by MC148p but rather selective inhibition of CCR8 activation by I-309 induced calcium mobilization assays and inhibition of I-309 induced chemotaxis assays (Luttichau H R et al. "A highly Selective CC Chemokine Receptor (CCR)8 Antagonist Encoded by the Poxvirus Molluscum Contagiosum J Exp Med 191:171-179, 2000).

1. Compositions According to the Present Disclosure

The disclosure relates to compositions adapted for the treatment of Atopic Dermatitis (AD), other atopic diseases, other inflammatory disorders, Th2 mediated disorders, and CCR8 mediated disorders. These compositions comprise a protein or sequence of amino acids selected from the group consisting of: MC148p1, MC148p2, MC148p3, other MC148p type proteins, MC148fp (fusion protein)1, MC148fp2, MC148fp3, other MC148fp type proteins, and fragments, variants, analogs, or derivatives of these proteins which possess AD inhibiting activity, human skin penetration capacity and/or exhibiting inhibition of chemotaxis and/or function of cells expressing CCR8.

A. Fragments of MC148p: Fragments of MC148p may be any amino acid sequence which is identical to or sufficiently homologous to MC148p such that AD inhibiting activity, human skin penetration capacity and/or CCR8 blocking activity is/are preserved. These fragments may be generated by genetic engineering, such as of translation stop sites within the coding region. These fragments may be formed using techniques known in the art, such as genetic engineering (e.g. in E. coli, baculovirus, etc.). Such materials may be made as a single peptide, a multimer which may be cleaved. Such materials may be obtained as a secreted material, through lysis of a cell, etc. and may be used directly or may be altered, such as refolded prior to use. Alternatively, treatment of the MC148p with proteolytic enzymes, known as proteases, can produce a variety of N-terminal, C-terminal and internal fragments. Examples of fragments may include contiguous portions of a MC148p of 6, 7, 8, 9, 10, 11, 12, 13, 14, 15, 16, 17, 18, 19, 20, 21, 22, 23, 24, 25-30, 31-35, 36-40, 41-45, 46-50, 51-55, 56-60, 61-65, 66-70, 71-75, 76-80, 81-85, 86-90, 91-95, 96-100, or more than 100 amino acids in length. These fragments may have primary, secondary (α-helices, β-sheets, or other), tertiary and quaternary structures, including domains and loops.

These fragments may be purified according to known methods, such as precipitation (e.g. ammonium sulfate), HPLC, ion exchange chromatography, affinity chromatography (including immune-affinity chromatography) or various size separations (sedimentation, gel electrophoresis, gel filtration).

B. Variants of MC148p: Variants of MC148p for inclusion in the compositions of the present disclosure can be substitution, insertion or deletion variants of MC148p. Deletion variants lack one or more residues of the native protein which are not essential for function or immunogenic activity, and are exemplified by the variants lacking a leader sequence. Another common type of deletion variant is one lacking secretory signal sequences or signal sequences directing a protein to bind to a particular part of a cell. Insertion mutants typically involve the addition of material at a non-terminal point in the polypeptide. This may include the insertion of an immune-reactive epitope or simply a single residue. Terminal additions, called fusion proteins have already been employed in this disclosure and are further discussed below.

Substitution variants typically contain the exchange of one amino acid for another at one or more sites within the protein, and may be designed to modulate one or more properties of the polypeptide, such as stability against proteolytic cleavage, without loss of other functions or properties. Substitutions of this kind preferably are conservative, i.e. one amino acid is replaced with another of similar shape and charge. Conservative substitutions are well known in the art and include, for example, the changes of: alanine to serine; arginine to lysine; asparagine to glutamine or histidine; aspartate to glutamate; cysteine or threonine to serine; glutamate to aspartate; glycine or leucine to proline; histidine to asparagine, lysine or glutamine; isoleucine to leucine or valine; leucine to valine; tyrosine to phenylalanine or tryptophan; the reverse of the above changes; other substitutions.

The following is a discussion based upon changing of the amino acids of a protein to create an equivalent, or even an improved, second-generation molecule. For example, certain amino acids may be substituted for other amino acids in a protein structure without appreciable loss of interactive binding regions of antibodies or binding sites on substrate molecules. Since it is the interactive capacity and nature of a protein that defines that protein's biological functional activity, certain amino acid substitutions can be made in a protein sequence, and it's underlying DNA coding sequence, and nevertheless obtain a protein with like properties. It is thus contemplated by the inventor that various changes may be made in the DNA sequences of genes without appreciable loss of biologic utility or activity.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982). These are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); arginine (−4.5).

Certain amino acids may be substituted by other amino acids having a similar hydropathic index or score and still result in a protein with similar biologic activity, i.e. still obtain a biologic functionally equivalent protein. In making such changes, the substitution of amino acids whose hydropathic indices are within +/−2 is preferred, those within +/−1 are particularly preferred and those within +/−0.5 even more particularly preferred.

The substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biologic property of the protein. As detailed in U.S. Pat. No. 4,554,101, the following hydrophilicity values have been assigned to amino acid residues: arginine (+3.0); lysine (+3.0); aspartate (+3.0+11); glutamate (+3.0+/−1); serine (+0.3); asparagine (+0.2); glutamine (+0.2); glycine (0); threonine (−0.4); proline (−0.5+/−1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent and immunologically equivalent protein. In such changes, the substitution of amino acids whose hydrophilicity values are within +/−2 is preferred, those that are with +/−1 are particularly preferred, and those within +/−0.5 are even more particularly preferred.

As outlined above, amino acid substitutions are generally based on the relative similarity of the amino acid side-chains, for example, their hydrophobicity, hydrophilicity, charge, size, and the like. Exemplary substitutions that take variants of the foregoing characteristics into consideration are well known to those of skill in the art and include: arginine and lysine; glutamate and aspartate; serine and threonine; glutamine and asparagine; and valine, leucine and isoleucine.

Another embodiment for the preparation of polypeptides according to the disclosure is the use of peptide mimetics. Mimetics are peptide-containing molecules that mimic elements of protein secondary structure. (See, for example, Johnson et al. "Peptide Turn Mimetics: in Biotechnology and Pharmacy. Pezzuto et al. Eds., Chapman and Hall, N.Y. 1993). The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used, in conjunction with the principles outlined above, to engineer second generation molecules having many of the natural properties of MCV type 1, type 2 and other type viral proteins, but with altered and even improved characteristics.

A specialized kind of variant (terminal addition) is the fusion protein. This molecule generally has all or a substantial portion of the native molecule, linked at the N- or C-terminus, to all or a portion of a second polypeptide. For example, fusions may employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or trans-membrane regions. The above proteins, fusion proteins, fragments, variants, analogs and derivatives for use in the compositions of the present disclosure can be produced by means of recombinant expression.

Figure 7A:
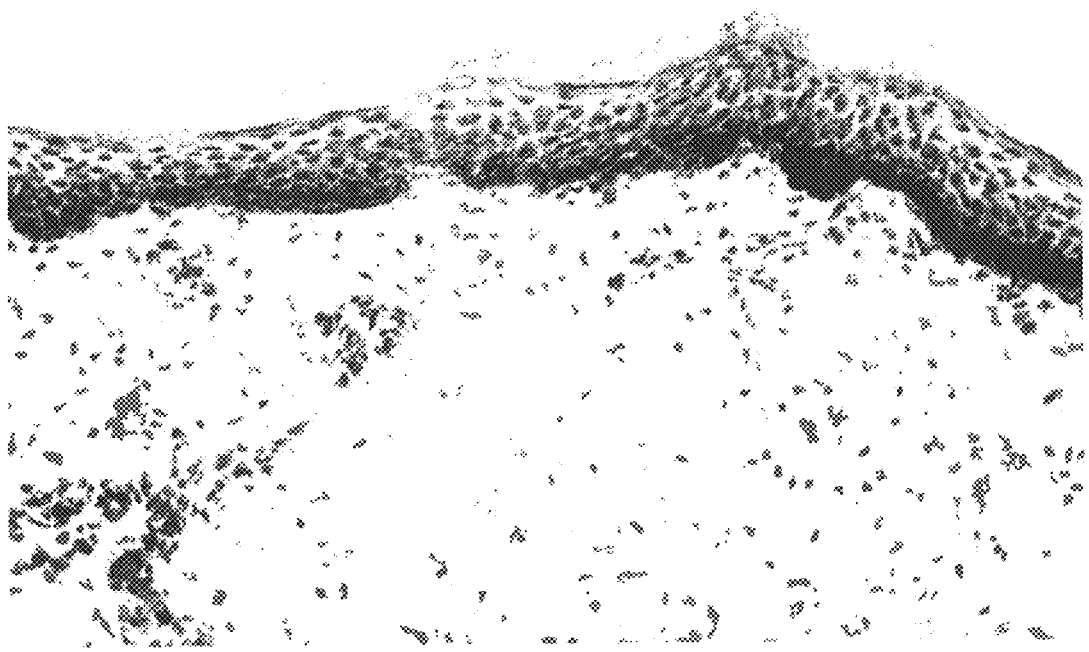
FIG. 7A illustrates by means of immunohistochemistry, using 6×His (SEQ ID NO: 11) antibody, the penetration of MC 148 fusion protein through the stratum corneum and its concentration along the basal cell layer of the epidermis.

One aspect of the invention provides a fusion protein (e.g. constructed as in FIG. 4B) to enable penetration of MC of the index case into skin, such as neonatal foreskin (FIG. 7A). This fusion protein has attached to the carboxyl terminal of MC148p1 of the index case the TAT sequence (tyrosine, glycine, arginine, lysine, lysine, arginine, arginine, glutamine, arginine, arginine, arginine or YGRKKRRQRRR (SEQ ID NO: 12)) followed by polyHis (such as 6×His (histidine, histidine, histidine, histidine, histidine, histidine or HHHHHH)) (SEQ ID NO: 11) at the C-terminus. A 6×His (SEQ ID NO: 11) provides an antigen for a (biotinylated) antibody; thus penetration of the fusion protein into human neonatal foreskin (or any other tissue or cells) can be proven such as in this instance by biotin streptavidin DAB immunohistochemistry (FIG. 7A). While not wishing to be limited to a particular mechanism, the TAT sequence enables penetration. This demonstration is an advance, for example, over the published work of Johnson J L et al. "TAT-Mediated Delivery of a DNA Repair Enzyme to Skin Cells Rapidly Initiates Repair of UV-Induced DNA Damage" J Invest Dermatol 131:753-761, 2011 in that Johnson J L et al. used a human full thickness skin model, Epi-derm FT (Mattek, Ashland, Mass. Such models have been called "human skin equivalents," but they are not equivalent. Artificial skin constructs have been shown to differ from real skin biochemically and structurally. For example, biochemically the stratum corneum of the artificial constructs studied by Thakoersing V S et al. (J Invest Dermatol 144:59-67, 2013) contains monounsaturated fatty acids, which enhance or induce the formation of hexagonal lateral packing of cornified cells (stratum corneum keratinocytes). Hence, such an artificial skin constructs mainly has a hexagonal packing. Hexagonal packing has been correlated with impaired barrier function, which in turn facilitates penetration of compounds whose penetration differs from penetration of compounds into normal stratum corneum. In addition, commercially sourced artificial constructs may not possess the classic 9 ceramide classes nor the 12 ceramide subclasses more recently identified (Thakoersing V S et al., Bouwstra J A in J Invest Dermatol 133: 59-67, 2013). By contrast normal human skin has a dense orthorhombic packing. The mainly hexagonal packing of artificial skin constructs that may correlate with impaired barrier function may have eased the penetration of the topically applied ~18 kDa protein studied by Johnson J L et al. referenced above. In contrast with the artificial skin test system used above, normal stratum corneum was used for testing according to the current disclosure, and significant penetration of therapeutic protein was achieved. It was by no means obvious that penetration of normal stratum corneum could be achieved.

One aspect of the invention described herein is that penetration of a topically applied protein of ~15.6 kDa into normal human neonatal skin has been achieved. The C-terminal polyHis (6×His (SEQ ID NO: 11)) may be retained. The positive charge of the histidine residues may further enhance penetration; further polyHis (e.g. 6×histidine (SEQ ID NO: 11)) may additionally provide a therapeutic benefit. Adult volunteers with AD fed L-histidine orally had a 34% improved SCORAD at the end of 4 weeks of treatment. No side effects were identified (Griffiths C E and Gibbs N K J Invest Dermatol 132:S51, 2012). As described herein, and as applied to the treatment of AD, the histidine residues may be being applied exactly where they are needed. A series of residues may be placed in or at any part of the fusion protein such as at the N-terminal, at the C-terminal, or in the middle of the protein (e.g., for example, between protein domains). The residues may, for example be useful as spacer residues or may provide a more specific benefit based on their composition. In some embodiments, the residues may be acidic residues. The acidic residues may include any number and any type of acidic residues (e.g. histidine residues, lysine residues or arginine residues), alone or in combination and in any pattern (e.g. alternating, random, etc.). 1, 2, 3, 4, 5, 6, 7, 8, 9, 10, from 10 to 20 (inclusive), from 21 to 30 (inclusive) or more than 30 such residues may be added. One or more than one (e.g. 2, 3, 4, or more than 4) such strings may be included in a Molluscum contagiosum fusion protein.

C. Administration to a Patient: Compositions according to the present invention, for the treatment of AD, other atopic diseases, other inflammatory disorders, Th2 mediated disorders and CCR8 mediated disorders may include one or more pharmaceutically acceptable carriers to provide a pharmaceutically acceptable composition for delivery to a patient. The phrase "pharmaceutically or pharmacologically acceptable" refers to molecular entities and compositions that are unlikely to produce adverse, allergic or other untoward reactions when administered to an animal or a human patient. As used herein, "pharmaceutically acceptable carrier(s)" includes any and all solvents, suspensions, dispersion media, coatings, oils, antibacterial and antifungal agents, preservatives, detergents, emollients, astringents, ointments, creams, lotions, gels, foams; occlusion techniques; iontophoresis, electroporation or other devices; isotonic and absorption delaying agents and the like, including the types of carriers referenced by Smith E W and Maibach H I: "Percutaneous Penetration Enhancers", CRC Press, 1995, N.W. Boca Raton, Fla. as well as other carriers described in the medical and technical literature. Methods contemplated for delivery of the composition are not limited to chemical penetration enhancers, but also include non-chemical methods such as iontophoresis and electroporation. A composition (e.g. containing a Molluscum contagiosum viral fusion protein as described herein) may be absorbed to, attached to, conjugated to, encapsulated in, or otherwise incorporated into or otherwise connected with another material. Such a material may provide any benefit, such as improved delivery of the composition to the body, reduced toxicity in the body, improved composition stability, etc. Such a material may be chemically neutral, negatively charged or positively charged. A positively charged material, may, in particular, aid penetration of a composition through the skin barrier (stratum corneum). Such a particle may be, for example, a microsphere or a nanoparticle. Such a particle may be less than 1 nm in at least one dimension, less than 10 nm in at least one dimension, less than 100 nm in at least one dimension, from 10 nm up to 50 nm in at least one dimension, from 50 nm up to 100 nm in at least one dimension, from 100 nm up to 500 nm in at least dimension, from 500 nm up to 1000 nm in at least one dimension, or longer than 100 nm or larger in at least one dimension. Such a particle may include any material that improves the composition, such as an alginate, alginate-chitosan, albumin, chitosan, gelatin, another polymer, a silicon particle, etc. In some embodiments, a fusion protein as described herein may be attached to a nanoparticle that is less than 500 nm in at least one dimension. In a particular example, fusion protein (e.g. an MC148fp as described herein) may be attached to positively charged alginate-chitosan nanoparticles which may enable penetration of the composition through the stratum corneum. Preferred pharmaceutically acceptable carriers include sulfoxides such as decylmethylsulfoxide, dimethylsulfoxide, pyrrolidones and combinations of these (Azone), macromolecular microspheres, liposomes and hydrogels.

Supplementary active ingredients also can be incorporated into the compositions. The use of such carriers and penetration enhancers for pharmaceutically active ingredients is well known in the art.

The pharmaceutically acceptable compositions of the present invention may include any classical or non-classical pharmaceutical preparation, which includes a MC148p, a MC148fp or a fragment, variant, analog or derivative of a MC148p or MC148fp as an active ingredient. Administration of these compositions according to the present invention will be via any common route so long as the target tissue is available via that route. Because the treatment of skin disease is initially contemplated, the route is preferably adapted for the treatment of skin, e.g. a localized delivery, optionally topically or via subcutaneous injection.

When the composition is delivered topically, the composition is preferably applied directly to the area affected by the skin disease. For subcutaneous or other administration, the most desirable point of delivery need not necessarily be at or near the area affected by the skin disease.

The pharmaceutically acceptable compositions according to the present invention may include sterile aqueous solutions or dispersions or suspensions for the preparation of sterile injectable solutions or dispersions. The form may be sterile and may be fluid in embodiments where the fluid is to be delivered by injection. The form should be stable under the conditions of manufacture and storage and may be preserved against contamination of microorganisms, such as bacteria, fungi and yeasts. The carrier can be a solvent or dispersion medium containing, e.g. water, ethanol, polyol (such as glycerol, propylene glycol, liquid polyethylene glycol and the like), suitable mixtures thereof, and vegetable or other oils. Proper fluidity can be maintained, by way of example, by the use of a coating, such as lecithin, by the maintenance of the required particle size in the case of dispersion and by the use of surfactants. The prevention of the action of micro-organisms can be brought about by various antibacterial, antifungal and anti-yeast agents, e.g. parabens, chlorobutanol, phenol, sorbic acid, thimerosal, benzalkonium and the like. In many cases, it may be preferable to include isotonic agents, e.g. sodium chloride, phosphate buffered saline or sugars. Prolonged adsorption of the injectable compositions can be brought about by the use in the compositions of agents delaying absorption, e.g. aluminum monostearate and gelatin.

Sterile injectable solutions may be prepared by incorporating the active ingredients in the required amount in the appropriate solvent with a variety of the other ingredients enumerated above, as required, followed by filtered sterilization. Generally, dispersions may be prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile filtered solution thereof.

The compositions of the present invention may be formulated in a neutral or salt form. Pharmaceutically acceptable salts include acid addition salts (formed with the free amino groups of the protein) which are generally formed with inorganic acids such as hydrochloric or phosphoric acids, or organic acids such as acetic, oxalic, tartaric, mandelic acids and the like. Base addition salts are salts formed with free carboxyl groups as derived from inorganic bases such as sodium, potassium, ammonium, calcium, or ferric hydroxides, and such organic bases as isopropylamine, trimethylamine, histidine, procaine and the like.

Upon formulation, solutions may be administered in a manner compatible with the dosage formulation and in such amount as is therapeutically effective. The formulations are easily administered in a variety of dosage forms such as injectable solutions, and the like. For parenteral administration in an aqueous solution, for example, the solution may be suitably buffered if necessary and the liquid diluent first rendered isotonic with sufficient saline or glucose. In this connection, sterile aqueous media, which can be employed, will be known to those of skill in the art in light of the present disclosure. For example, one dosage could be dissolved in 1 ml of isotonic NaCl solution and either added to 1000 ml of hypodermoclysis fluid or injected at the proposed site of infusion (see for example, "Remington's Pharmaceutical Sciences" $15^{th}$ Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations meet sterility, pyrogenicity, general safety and purity standards such as required by the FDA Office of Biologics Standards.

2. Descriptions of FIGS. 5A-8B.

Figure 5A:
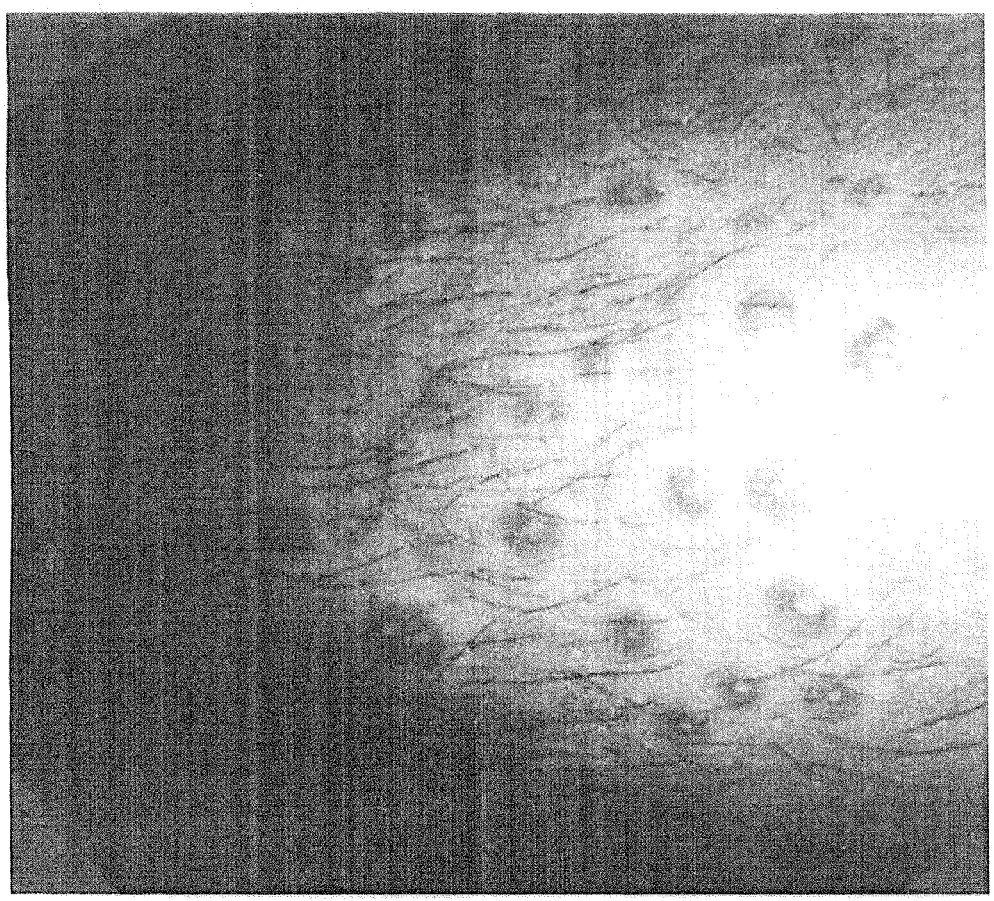
FIG. 5A illustrates the clinically demonstrable inhibitory effect of MCV upon a field of AD at a focal distance of 15 centimeters.
Figure 5B:
FIG. 5B illustrates the clinically demonstrable inhibitory effect of MCV upon a field of AD at a focal distance of 5 centimeters.

FIGS. 5A-5B illustrate the clinically demonstrable inhibitory effect of MCV upon a field of AD.

In FIGS. 5A and 5B the patient (PR) is a light skinned African American man, 16 years of age at the time these photographs were taken. PR had a chronic, widespread, waxing and waning atopic dermatitis (AD). He carried a persistent and heavy infection of Molluscum contagiosum virus (MCV) expressed as numerous light reddish tan, mildly lucent, sometimes umbilicated papules (hillocks) shown on the clinical photographs. The papules consisted of MCV infected epidermal keratinocytes. Many of the papules were ~5 mm in diameter (range 3 to 7 mm).

FIG. 5A photograph was taken at a focal distance of 15 centimeters and FIG. 5B photograph at 5 centimeters. FIG. 5A shows a background of AD manifest as mildly scaly, somewhat lichenified, reddish brown skin. Clear zones of clinically normal skin surround each papule of MCV. The clear zones range from 3 to 8 mm in dimension from the edge of a MCV papule to the edge of the background dermatitis. There appears to be a rough correlation between the size of a MCV papule and the width of the clear zone around it. The lack of a direct linear correlation could be associated with colonization of the skin with *Staphylococcus aureus* (Staph or *S. aureus*).

Staph frequently colonizes the skin of patients with AD and almost invariably exacerbates the dermatitis. PR had culture proven *S. aureus* skin infections. AD is characterized by the expression of the ligand I-309 (CCL 1) induced recruitment to the skin of cells expressing CCR8. Chemokine ligand I-309 is not found expressed in normal skin but shows a marked staining within the basal cell layer of the epidermis in patients with AD and is in large measure produced by Langerhans cells and endothelial cells. (Gombert M et al. "CCL1-CCR8 Interactions: An Axis Mediating the Recruitment of T Cells and Langerhans-Type Dendritic Cells to Sites of Atopic Skin Inflammation" J Immunol 174:5082-5091, 2005). The recruited cells include activated Th2 cells, dermal dendrocytes and epidermal Langerhans cells. Serum levels of I-309 are markedly elevated in patients with severe AD and correlate with numbers of eosinophils in peripheral blood of these patients, suggesting that eosinophils might also express CCR8 (Higashi N et al. in J Invest Dermatol 125:601, 2005), because I-309 is a specific chemokine for CCR8. (Luttichau H R et al. in J Exp Med 191:171-179, 2000). Indeed the paucity of inflammatory cells, including eosinophils, as well as a dearth of capillaries in the clear zones adjacent to the MCV papules as shown clinically in FIGS. 5A and 5B and microscopically in FIG. 6A suggest that endothelial cells, eosinophils, activated Th2 cells and cells of the monocyte line, including dendrocytes and Langerhans cells all express CCR8 in AD inflamed skin. All of this is aggravated by S. aureus because S. aureus induces production of I-309 from mast cells, dendrocytes and endothelial cells. Further S. aureus exotoxins up-regulate T cell production of the highly pruritogenic IL-31 which is also elevated in patients with AD.

FIG. 5B shows a photograph of an area of more severe AD in patient PR—an area characterized by a dark gray brown, markedly lichenified skin with prominent scale. Four frank excoriations are demonstrable. (Persons with AD almost always itch and almost always scratch.) In the center of the photograph are 2 MCV papules around which are clear zones of normal appearing skin. Hence the anti-inflammatory effect of MCV is sufficiently powerful to suppress even severely inflamed atopic dermatitis.

The zone of inhibition around each MCV papule may be viewed as analogous to the zone of inhibition around a penicillin disk on an agar plate streaked with Streptococci. The therapeutic implications are also analogous.

FIGS. 6A-6B illustrate the microscopically demonstrable inhibitory effect of MCV upon a field of AD. The photomicrograph of the biopsy depicted in FIG. 6A was taken from an area of atopic dermatitis on the skin of PR immediately adjacent to a papule of MCV. The edge of the papule is seen on the lower left, and within the expanded lower spinous cell layer of the papule, the cytoplasm of the keratinocytes contains Molluscum bodies, visible on light microscopy as deposits of eosinophilic amorphous material. The top of the photomicrograph shows the base of the adjacent epidermis. Moderate numbers of fibroblasts are found in a modified connective tissue around the Molluscum papule. A paucity of mononuclear cells is found around sparse small capillaries in the upper part of the dermis adjacent to the Molluscum papules. There is a mild to moderate acanthosis, seen here in the lower part of the epidermis. Scant is the inflammatory infiltrate within the connective tissue in the region of the Molluscum papule, extending far laterally into the papillary and reticular parts of the dermis. The lack of inflammation in the dermis adjacent to the Molluscum papule resembles the appearance of normal skin. (H&E, 100).

The photomicrograph of the biopsy depicted in FIG. 6B was taken concurrently (the same date and time) from a similar area of AD on the skin of PR remote from the Molluscum papules grouped and scattered on his skin. The top of the photomicrograph shows a markedly acanthotic epidermis with a central adherent crust denoting a site of excoriation, due to incessant itching characteristic of AD. The itching, in turn, is secondary to inflammatory mediators of diverse origing—many of which are the products of the inflammatory cells which infiltrate the skin of patients with AD. The moderate to marked, predominantly lymphohistiocytic infiltrate is seen here not only around the blood vessels of the superficial plexus, but also around vessels of the upper reticular dermis serving that plexus and around vessels of the papillae. The infiltrate of inflammatory cells extends into the interstitium. Inflammatory cell epidermotropism is also present. (H&E, 100×). At higher magnification, eosinophils can also be seen within the inflammatory infiltrate on this photomicrograph.

FIG. 7A illustrate the penetration of MC148 fusion protein (MC148p-TAT-6×His ("6×His" disclosed as SEQ ID NO: 11)) through the stratum corneum of normal neonatal skin and its accumulation along the basal cell layer. Lighter deposits of MC148p-TAT-6×His ("6×His" disclosed as SEQ ID NO: 11) are seen in the stratum corneum and elsewhere in the malpighian layer. Penetration was achieved using concentrations as low as 3 μg of fusion protein in 100 μL of phosphate buffered saline (PBS), applied in separate experiments in aliquots of 20 μL and later 10 μL to be sure that no solution seeped around the edges of the neonatal foreskins on the undersurfaces. Concentration of 30 μg in 100 μL of PBS enabled penetration of MC148-TAT-6×His ("6×His" disclosed as SEQ ID NO: 11). The use of higher and lower concentrations is not excluded. For example, from 0.1 μg up to 1 μg, from 1 μg up to 5 μg, from 2 μg up to 4 μg, from 5 μg up to 10 μg, from 10 μg up to 50 μg, from 50 μg up to 300 μg, or more than 300 μg, in 100 μL of PBS may be used.

Figure 7B:
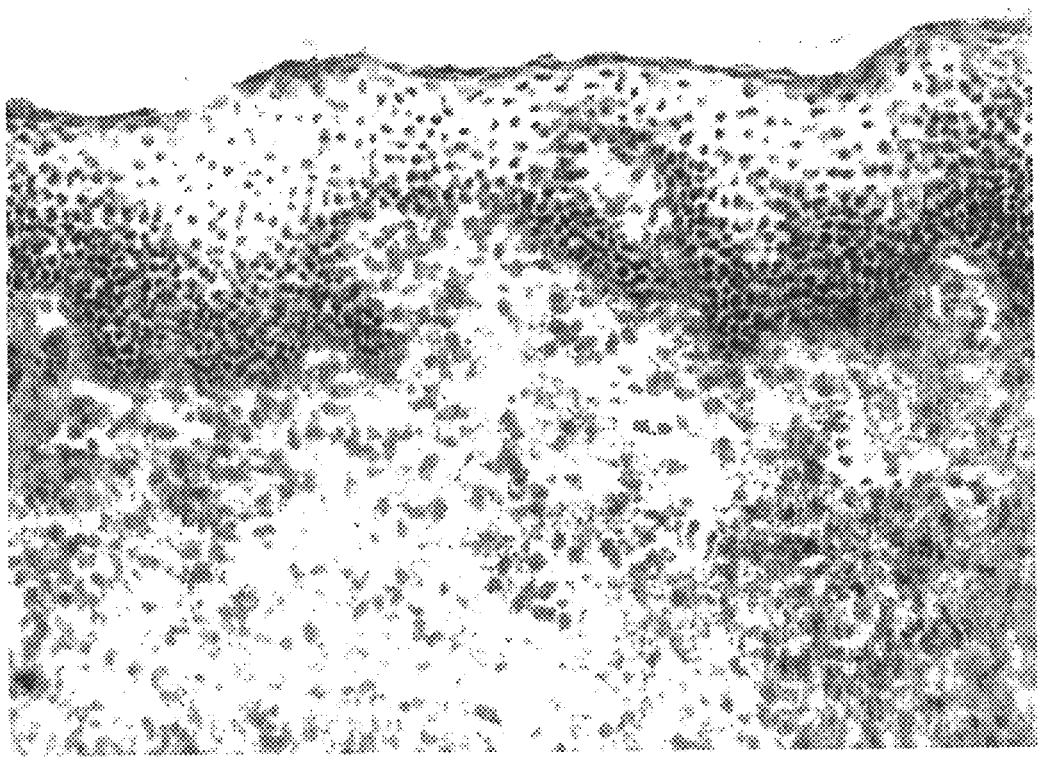
FIG. 7B illustrates by means of immunohistochemistry, using Collagen 1A antibody and omitting 6×His (SEQ ID NO: 11) antibody, both positive and negative controls.

FIG. 7B illustrates both positive and negative controls. Anti-Collagen 1A antibody tagged with biotin was applied to the foreskins in the process of standard immunohistochemical procedure giving the positive control whereas anti-His antibody tagged with biotin was not used providing the negative control.

Neonatal foreskins were chosen for penetration studies because their properties approximate the properties of atopic dermatitis (AD) lesional skin. Both neonatal skin and AD skin have low hydration and are susceptible to irritants and allergens. The concentration of natural moisturizing factor is significantly lower in neonatal and AD skin than in normal human adult skin. Two key enzymes of lipid processing to form ceramides (β-glucocerebrosidase and acid sphingomyelinase) do not have the required acidic pH for optimal activity, resulting in impaired formation of ceramides in neonatal stratum corneum and defective barrier function. Further the neutral to alkaline pH of neonatal skin amplifies the activity of serine proteases (kallikreins 5 and 7) which block lamellar body secretion of stratum corneum lipids, further impairing barrier function (Fluhr J W in Br J Dermatol 166:483-490, 2012). These impairments are also characteristic of lesional skin of AD.

MC148p inhibits I-309 induced chemotaxis of cells expressing CCR8 at very low concentrations (IC50 2 nM). However, MC148p shows no penetration of neonatal stratum corneum after repeated attempts. The McCullough group achieved penetration of their Chlorella virus-pyrimidine-dimer-glycosylase by attaching a nuclear localization sequence (NLS) and a transcriptional transactivator peptide (TAT) derived from the human immunodeficiency virus, yielding a fusion protein whose molecular weight was ~18 kDa (Johnson J L, see below). For penetration studies the McCullough group (Johnson J L, as below) used a synthetic commercially available full thickness human skin model, Epi-derm FT (Matttek, Ashland, Mass.), and by fluorescent probes showed penetration of Cv-pdg-NLS-TAT into the skin model, with its accumulation along the basal cell layer. (Johnson J L, Lowell B C, Ryabinina O P, Lloyd R S and McCullough A K "TAT-Mediated Delivery of a DNA Repair Enzyme to Skin Cells Rapidly Initiates Repair of UV-Induced DNA Damage" J Invest Dermatol 131:753-761, 2011).

A therapeutic protein characteristically targets (only) the extracellular space. In order to deliver a therapeutic protein further, a specific arginine-rich protein transduction sequence from antennapedia, TAT, VP22, etc. was used to deliver proteins into cells by attaching the arginine-rich transporter peptides to cysteine groups within such proteins. Success of this delivery method was shown by biologic effects such as induction of apoptosis by delivery of caspase-3 (Siprashvili Z, Reuter J and Khavari P in J Invest Dermatol 122: A51, 2004). Fluid phase endocytosis was shown to be "the" mode of cellular entry of the protein transduction domain of TAT (Gump J M, Dowdy S F in Trends Mol Med 13: 443-8, 2007). This approach is not germane to skin barrier penetration which is described herein. For example, fluid phase endocytosis is very different from the delivery of a protein through the stratum corneum, as described herein.

The stratum corneum is a dead, tough and resistant skin barrier making up the outer layer of the skin. It separates and protects underlying tissue from environmental factors, such as bacteria, other infectious agents, chemicals, debris, toxins and (other) proteins. It also provides a barrier to prevent a desired therapeutic agent from entering the body. It is not a cell membrane (e.g. it is not a cell in the interstitial fluid) but rather it is a compact barrier of lipid and keratin. Classically unaided absorption of molecules through the stratum corneum barrier of intact human skin is limited to molecules smaller than about 500 Da (Bos and Meinardi, Exp Dermatol 9:165-169, 2000) and favors lipophilic compounds. Hydrophilic drugs penetrate the stratum corneum poorly or not at all, presumably due (at least in part) to the lipophilic properties of the stratum corneum. For example, Gobel A, Schmaus G, Wohlrab J et al., J Am Acad Dermatol. 60: AB82, 2009) describes achieving penetration of a peptide consisting of 2 amino acids through the stratum corneum using 5% 1, 2 pentanediol to increase the penetration of the dipeptide carnosine. By contrast, this disclosure demonstrates penetration of a peptide consisting of 121 amino acids with a molecular weight approximating 15.6 kDa.

Challenges in treating a body (such as the skin) with a topical compound may include determining a useful therapeutic agent, generating a useful (active) therapeutic agent, maintaining the agent's stability (e.g. ensuring a useful shelf life), and delivering (e.g. applying) the agent to the body such as to the skin. Additional challenges may include transporting the agent across the stratum corneum, such as by passively diffusing it across the stratum corneum (such as allowing it to diffuse) or by actively transporting it (such as using an electric field or electric current). Further challenges may include delivering the agent through the interstitial fluid (such as to a cell), moving the agent to the outside of a cell, moving an agent across the cell membrane, and effecting a change by the agent (e.g. by maintaining a therapeutic activity or activating a therapeutic activity), such as on a molecule or a cell. Further challenges may include enabling the treatment in an individual with an abnormal skin composition (e.g. an altered barrier composition such as in an atopic dermatitis patient) or an altered immunological state. In addition to needing to overcome such obstacles, the behavior of a given peptide or protein varies widely from another peptide or protein in the same environment. The behavior of a single peptide or protein varies from one environment to another, making it difficult to predict based on the behavior of one protein type how another protein will behave. Such differences may be obvious or may be seemingly small that nonetheless control the protein's behavior in any given environment as exemplified by such variables as overall length, folded size, overall charge, hydrophobicity or hydrophilicity, local or domain charge, hydrophobicity or hydrophilicity, the particular cell type or extracellular environment. For example, Wolf P., Yarosh D., and Kripke M L (J Invest Dermatol 114: 149-56, 2000) used liposomes to encapsulate the viral nucleic acid repair enzyme, T4 endonuclease V which is approximately 16.5 kDa. Encapsulating biotinylated MC148 protein in liposomes following the Yarosh method achieved about 90% encapsulation efficiency. However, neonatal foreskin experiments with MC 148 protein in PBS did not show penetration. Yarosh enhanced delivery of the proteinated liposomes in a specific hydrogel called Hypan S S 201 (Vladimir Stoy and Charles Kliment); however, Hypan S S 201 is no longer available. Such approaches could not be readily used to deliver MC148 to the cells of interest.

One aspect of the invention, such as illustrated in FIG. 7A, is a hydrophilic fusion protein (MC 148p-TAT-6×His ("6× His" disclosed as SEQ ID NO: 11)) weighing ~15.6 kDa that penetrates the intact skin barrier (including the stratum corneum) of normal human neonatal skin. This is both new and unexpected. There are significant differences between the work done by the McCullough group and the subject of this disclosure. In addition to using different protein/peptide sequences, different targets, etc. in the McCullough fusion protein, the TAT penetration enabling sequence was positioned at the carboxyl terminus of the protein, whereas as described in some embodiments of the disclosure herein, the TAT sequence is separated from the carboxyl terminus by histidine residues (e.g. by 6 histidine residues (SEQ ID NO: 11), to form an MC 148p-TAT-PolyHis protein. The McCullough group used an artificial skin construct. Such constructs have been called "human skin equivalents," but they are not equivalent. Artificial skin constructs have been shown to differ from real skin biochemically and structurally. Artificial constructs contain monounsaturated fatty acids, such as oleic acid possessing one double bond, which enhance the formation of hexagonal lateral packing. As mentioned, these artificial skin constructs have been shown mainly to display hexagonal packing, which corresponds to impaired barrier function (Thakoersing V S et al. in J Invest Dermatol 133:59-67, 2013). By contrast, normal human skin contains primarily polyunsaturated fatty acids such as linoleic acid possessing 2 double bonds which correspond to a dense orthorhombic packing and normal barrier function. The histidine (e.g. 6×His (SEQ ID NO: 11)) does not appear to substantially interfere with passage of MC148p-TAT into the skin. It rather may enhance penetration through the stratum corneum, perhaps due to its positive charge. In addition to this, polyHis may have therapeutic advantage in the treatment of AD independent of the anti-inflammatory action of the MC148 portion of the fusion protein. Adult volunteers with atopic dermatitis fed L-histidine orally had alleviation of their atopic dermatitis as demonstrated by a 34% improved SCO-RAD at the end of 4 weeks and a 19% reduction in transepidermal water loss (TEWL). No side effects were identified (Griffiths C E and Gibbs N K J Invest Dermatol 132:S51, 2012).

Figure 8A:
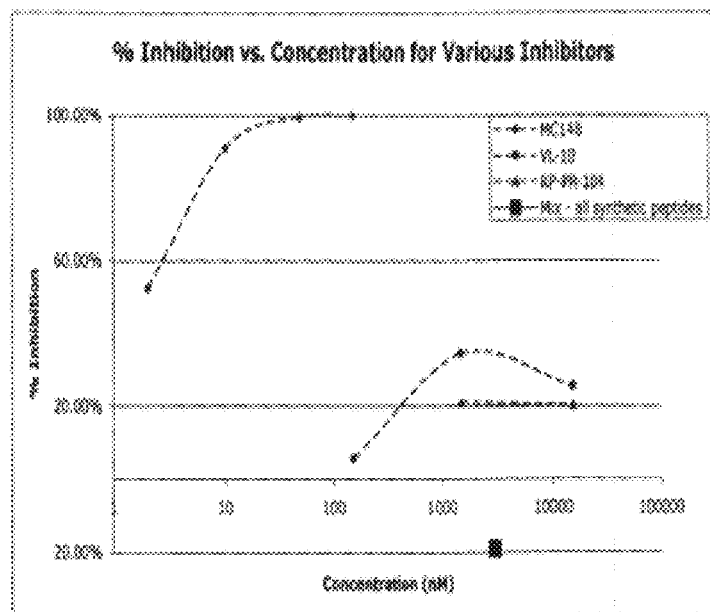
FIG. 8A illustrates I-309 induced chemotaxis inhibited by recombinant MC 148 protein with an IC50 at about 2 nM whereas synthetic MC 148 protein fails to obtain an IC50 even at 15,000 nM.

FIG. 8A illustrates that I-309 induced chemotaxis is inhibited by recombinant MC148 protein with an IC50 at ~2 nM whereas synthetic MC 148 protein fails to obtain an IC50 even at 15,000 nM. FIG. 8A also shows that the peptide fragment VL-10 consisting of amino acids VSLARRKCCL (SEQ ID NO: 13) and encompassing the binding site of MC148p also fails to obtain an IC50 at 15,000 nM. Finally FIG. 8A shows that a mix of all synthetic peptides tested—all encompassing the binding site of MC148p—had a negative inhibitory effect, i.e. behaved in a manner to exacerbate inflammation. The composition of the mix of fragments was as follows: VL-10 as above, PP-20 consisting of amino acids PRPGVSLARRKCCLNPTNRP (SEQ ID NO: 14), MP-38 consisting of the first 38 amino acids starting from the N-terminus (see FIG. 1B) and VV-54 consisting of the 54 amino acids starting with a valine at position 23 and extending to the valine at position 76 (see FIG. 1B). These results also inform that the entire recombinant protein may be especially effective in achieving an inhibitory (anti-inflammatory) effect. The fragments tested and the synthetic 104 amino acid synthetically made protein lack the proper folding required for biologic effect.

Figure 8B:
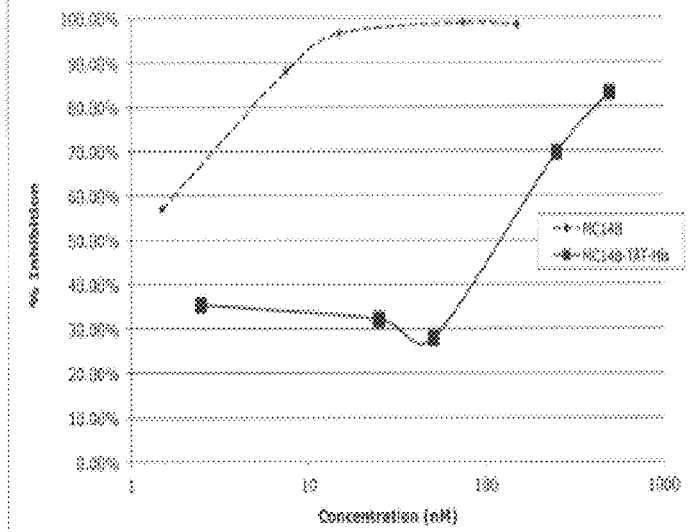
FIG. 8B illustrates I-309 induced chemotaxis inhibited by recombinant MC 148 fusion protein with an IC50 at about 200 nM.

The biological effect (e.g. functionality or activity) of adding one or more than one domain to a protein is unpredictable. It was unclear whether a protein comprising an MC 148 protein, a TAT portion and a polyHis portion would remain functional, such as on chemotaxis assays. In particular, it was predicted that the positive charges of both the TAT sequence and the 6×His sequence (SEQ ID NO: 11) added to the MC148 protein could interfere with the positive charges of the two arginines and the one lysine at positions 27, 28 and 29 respectively of MC148 protein (i.e. the sites at which MC 148 protein binds to CCR8 expressing cells to have a therapeutic effect). FIG. 8B illustrates that I-309 induced chemotaxis is inhibited by recombinant MC148p-TAT-6×His ("6×His" disclosed as SEQ ID NO: 11) with an IC50 at ~200 nM. This inhibitory capacity may be compared with that of MC148p suggesting that the positively charged amino acids of TAT and 6×His (SEQ ID NO: 11) at the carboxyl terminal may have partially interfered with the binding of the native recombinant MC148p to the receptor site of CCR8 near the amino terminals of both proteins. Yet MC148p-TAT-6×His ("6×His" disclosed as SEQ ID NO: 11) enables topical delivery which the unmodified MC148p does not. It is noted that the fusion protein (MC148p-TAT-6×His ("6×His" disclosed as SEQ ID NO: 11)) remains an effective inhibitor of cells expressing CCR8, albeit at higher but attainable concentration and is therefore suitable for functional testing in vivo.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural forms unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method for treating a patient having at least one of atopic dermatitis and an atopic dermatitis-related disease, comprising:
 administering topically to a patient having at least one of atopic dermatitis and an atopic dermatitis-related disease a therapeutically effective amount of a composition comprising a Molluscum contagiosum viral fusion protein MC148p-TAT-poly-His (MC148fp) which possesses at least one of atopic dermatitis inhibitory activity and an atopic dermatitis related disease inhibitory activity, wherein administering comprises passing the composition through a stratum corneum of the patient so that it accumulates along the basal cell layer.

2. The method according to claim 1, wherein administering to a patient comprises administering a MC148fp selected from the group consisting of Molluscum contagiosum viral fusion protein 148fp1 (MC148fp1) and Molluscum contagiosum viral fusion protein 148fp2 (MC148fp2), fused at its C-terminus with TAT and poly-His.

3. The method according to claim 2 wherein administering comprises administering an MC148fp selected from the group consisting of Molluscum contagiosum viral fusion protein 148fp1 (MC148fp1) and Molluscum contagiosum viral fusion protein 148fp2 (MC148fp2), fused at its C-terminus with TAT and 6×His (SEQ ID NO: 11) terminal to TAT.

4. The method according to claim 1, wherein administering the composition includes injecting the composition into the patient.

5. The method according to claim 1, wherein administering the composition includes electroporating the composition.

6. The method according to claim 1, wherein administering the composition further includes administering a skin penetration enhancement carrier.

7. The method according to claim 1, wherein administering the composition comprises administering nanoparticles with the composition.

8. The method according to claim 1, wherein administering the composition includes delivering the composition locally to an area of patient skin comprising at least one of atopic dermatitis and an atopic dermatitis-related disease.

9. The method according to claim 1, wherein administering the composition includes delivering the composition to an area of patient skin lacking atopic dermatitis and an atopic dermatitis-related diseases.

10. A method for treating a patient having a CC chemokine receptor 8 (CCR8) mediated disease, comprising:
 administering topically to a patient having a CCR8 mediated disease a therapeutically effective amount of a composition comprising a Molluscum contagiosum viral fusion protein MC148p-TAT-poly-His (MC148fp) which possesses a CCR8 inhibitory activity, wherein administering comprises passing the composition through a stratum corneum of the patient so that it accumulates along the basal cell layer.

11. A method for treating a patient having at least one of atopic dermatitis and an atopic dermatitis-related disease comprising:
 administering topically to a patient having at least one of atopic dermatitis and an atopic dermatitis-related disease a therapeutically effective amount of a composition comprising a Molluscum contagiosum viral fusion protein MC148p-TAT-poly-His (MC148fp) which possesses at least one of atopic dermatitis inhibitory activity and an atopic dermatitis-related disease inhibitory activity, wherein administering comprises passing the composition through a stratum corneum of the patient so that it accumulates non-exclusively along the basal cell layer.

* * * * *